(12) United States Patent
Yoshino

(10) Patent No.: US 11,534,411 B2
(45) Date of Patent: Dec. 27, 2022

(54) COMPOSITION FOR FORMING COATING FILM

(71) Applicant: KAO CORPORATION, Tokyo (JP)

(72) Inventor: Tatsuya Yoshino, Funabashi (JP)

(73) Assignee: KAO CORPORATION, Tokyo (JP)

( * ) Notice: Subject to any disclaimer, the term of this patent is extended or adjusted under 35 U.S.C. 154(b) by 88 days.

(21) Appl. No.: 16/966,957

(22) PCT Filed: Feb. 7, 2019

(86) PCT No.: PCT/JP2019/004359
§ 371 (c)(1),
(2) Date: Aug. 3, 2020

(87) PCT Pub. No.: WO2019/156146
PCT Pub. Date: Aug. 15, 2019

(65) Prior Publication Data
US 2021/0038530 A1 Feb. 11, 2021

(30) Foreign Application Priority Data

Feb. 8, 2018 (JP) .............................. JP2018-021365
Oct. 17, 2018 (JP) .............................. JP2018-195876

(51) Int. Cl.
*A61K 9/70* (2006.01)
*A61K 47/32* (2006.01)
(Continued)

(52) U.S. Cl.
CPC ............ *A61K 9/7015* (2013.01); *A61K 47/32* (2013.01); *A61K 47/44* (2013.01); *C08L 29/00* (2013.01)

(58) Field of Classification Search
None
See application file for complete search history.

(56) References Cited

U.S. PATENT DOCUMENTS 4,752,496 A * 6/1988 Fellows ............. A45D 40/0087
428/905
6,531,142 B1 3/2003 Rabe et al.
(Continued)

FOREIGN PATENT DOCUMENTS

EP 0 523 961 A1 1/1993
EP 3 613 411 A1 2/2020
(Continued)

OTHER PUBLICATIONS

International Search Report dated Mar. 26, 2019 in PCT/JP2018/004359 filed Feb. 7, 2019, 2 pages.
(Continued)

*Primary Examiner* — Melissa S Mercier
(74) *Attorney, Agent, or Firm* — Oblon, McClelland, Maier & Neustadt, L.L.P.

(57) ABSTRACT

Provided is a composition for forming a coating film directly on the skin by an electrostatic spray, the composition being capable of forming a coating film having excellent skin compatibility, adhesion, and scratch resistance, having a good feel, and being easy to peel. A composition for forming a coating film, for forming a coating film composed of fibers directly on the skin by an electrostatic spray, the composition comprising the following Components (a), (b), (c), and (d):
(a) a polymer having a coating film forming ability
(b) one or more volatile substances selected from the group consisting of an alcohol and a ketone
(c) a plasticizer
(d) a feel modifier other than Component (c).

35 Claims, 1 Drawing Sheet

(51) Int. Cl.
   *A61K 47/44* (2017.01)
   *C08L 29/00* (2006.01)

(56) References Cited

U.S. PATENT DOCUMENTS

| | | |
|---|---|---|
| 2001/0023902 A1 | 9/2001 | Wilson et al. |
| 2004/0086474 A1 | 5/2004 | Rabe et al. |
| 2016/0324298 A1* | 11/2016 | Samain ............... A61K 8/0233 |
| 2019/0053602 A1 | 2/2019 | Amari et al. |
| 2019/0059551 A1 | 2/2019 | Amari et al. |
| 2020/0155423 A1 | 5/2020 | Ito |

FOREIGN PATENT DOCUMENTS

| | | |
|---|---|---|
| JP | 54-140713 A | 11/1979 |
| JP | 7-82142 A | 3/1995 |
| JP | 10-287529 A | 10/1998 |
| JP | 2001-226240 A | 8/2001 |
| JP | 2003-507165 A | 2/2003 |
| JP | 2006-95332 A | 4/2006 |
| JP | 2006-104211 A | 4/2006 |
| JP | 2017-78062 A | 4/2017 |
| JP | 2017-78063 A | 4/2017 |
| WO | WO 01/12139 A1 | 2/2001 |
| WO | WO 2018/194084 A1 | 10/2018 |

OTHER PUBLICATIONS

Extended European Search Report dated Mar. 2, 2022 in European Patent Application No. 19750636.3, 11 pages.
Database GNPD [Online]—"Makeup Setting Spray", Mintel, Record ID: 3377203, Aug. 18, 2015, XP055578800, 3 pages.
"Air Touch Foundation", ID 600036, Mintel GNPD[online], Oct. 2016,[Retrieved on Mar. 2, 2022], Internet: https://www.portal.mintel.com, 11 pages.
"Veil Potion", ID 7131809,Mintel GNPD[online], Dec. 2019 [Retrieved on Mar. 2, 2022], Internet: https://www.portal.mintel.com, 9 pages.

* cited by examiner

COMPOSITION FOR FORMING COATING FILM

FIELD OF THE INVENTION

The present invention relates to a composition for forming a coating film directly on the skin by an electrostatic spray.

BACKGROUND OF THE INVENTION

Various methods are known for forming a coating film by an electrostatic spray. For example, Patent Literature 1 discloses a skin treatment method including electrostatically spraying a composition on the skin. The composition used in this method contains a liquid insulating substance, an electrically conducting substance, a particulate powder substance, and a thickener. This composition is typically used as cosmetic products containing a pigment and skincare compositions. Specifically, the composition is used as a makeup foundation. That is, the invention described in Patent Literature 1 mainly considers wearing a makeup on the skin by electrostatically spraying a makeup foundation for a cosmetic purpose.

Patent Literature 2 discloses a disposable cartridge to be used for an electrostatic spray apparatus of a cosmetic product. This electrostatic spray apparatus is a hand-held self-contained style. This electrostatic spray apparatus is used to spray a makeup foundation as in Patent Literature 1 described above.

Patent Literature 3 discloses a method for enhancing coating film adhesion by applying a solution before or after forming a coating film on the surface of the skin by an electrostatic spray method.

(Patent Literature 1) JP-A-2006-104211
(Patent Literature 2) JP-A-2003-507165
(Patent Literature 3) JP-A-2017-78062

SUMMARY OF THE INVENTION

The present invention relates to a composition for forming a coating film, for forming a coating film composed of fibers directly on the skin by an electrostatic spray, the composition comprising the following Components (a), (b), (c), and (d):
(a) a polymer having a coating film forming ability
(b) one or more volatile substances selected from the group consisting of an alcohol and a ketone
(c) a plasticizer
(d) a feel modifier other than Component (c).

DETAILED DESCRIPTION OF THE INVENTION

Figure 1:
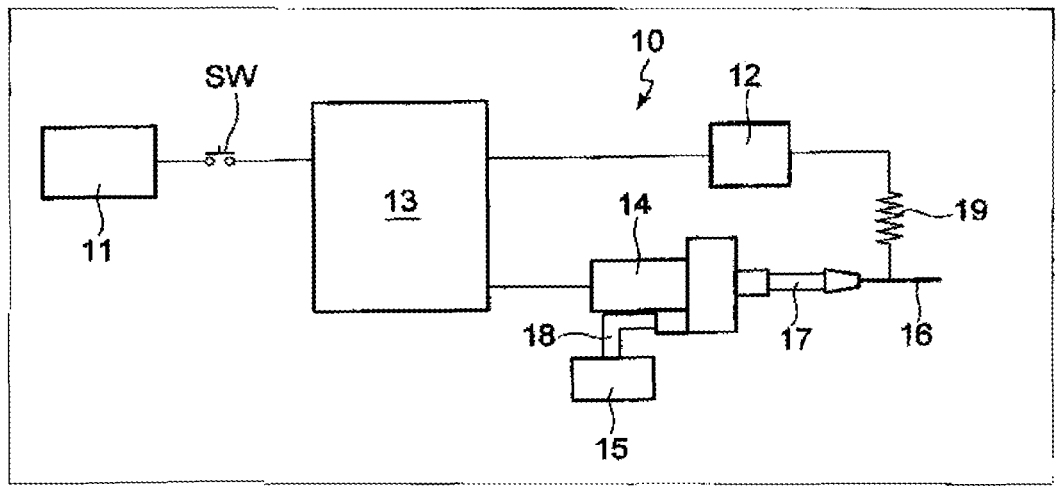
FIG. 1 illustrates a diagram showing a structure of the electrostatic spray apparatus preferably used in the present invention.

When a coating film is formed on the skin by carrying out an electrostatic spray in accordance with the methods described in Patent Literatures 1 and 2, the adhesion between the skin and the coating film formed by the electrostatic spray is not sufficient and hence the coating film may be damaged or peeled off due to an external force such as a friction. Additionally, when a coating film is formed on the skin by the method described in Patent Literature 3, the coating film adhesion is enhanced to a certain extent but further enhancements in the adhesion and scratch resistance are demanded, and the skin compatibility and a favorable feel are also demanded when an electrostatic spray is carried out on the skin to which a skincare cosmetic has been applied in advance. There was also room for improvement in the peelability of a coating film formed on the skin by an electrostatic spray.

Thus, the present invention relates to a composition for forming a coating film directly on the skin by an electrostatic spray, the composition being capable of forming a coating film having excellent skin compatibility, adhesion, and scratch resistance, having a good feel, and being easy to peel.

Accordingly, the present inventor conducted various studies on compositions for an electrostatic spray composition used for forming a coating film on the skin instead of a composition applied before or after forming a coating film on the skin by an electrostatic spray method, and found that when a plasticizer is used in combination with a feel modifier other than the plasticizer in addition to a polymer having a coating film forming ability and a volatile substance, the coating film formed directly on the skin by an electrostatic spray has excellent skin compatibility, adhesion, and scratch resistance and is easy to be peeled off despite having a good feel, whereby the present invention was accomplished.

When a coating film composed of fibers is formed directly on the skin by an electrostatic spray using the composition of the present invention, the obtained coating film has the characteristic of having excellent skin compatibility, adhesion, and scratch resistance, and is easy to be peeled off despite having a good feel. Additionally, when an electrostatic spray is carried out on the skin to which a skincare cosmetic has been applied in advance or when a skincare cosmetic is applied after a coating film is formed on the skin by an electrostatic spray, the skin compatibility with the coating film is extremely favorable.

The composition for forming a coating film of the present invention is a composition for forming a coating film composed of fibers directly on the skin by an electrostatic spray and contains Components (a), (b), (c), and (d) described above. The coating film composed of fibers in the present invention means a coating film containing the fibers of Component (a) and may also be a coating film in which, for example, a liquid substance is present around the fibers other than the fibers.

The polymer having a coating film forming ability, Component (a), is a substance generally soluble in the volatile substance of Component (b). Soluble herein refers to a state in which, when Component (a) and Component (b) are mixed, Component (a) is in a dispersed state in Component (b) at 20° C. and such a dispersed state is a visually homogenous state, and preferably a visually transparent or semitransparent state.

For the polymer having a coating film forming ability, a suitable polymer is used depending on the property of the volatile substance of Component (b). Specifically, the polymers having a coating film forming ability are roughly categorized into water-soluble polymers and water-insoluble polymers. The "water-soluble polymer" in the present Description refers to a polymer having a property that, under an environment of 1 atmosphere and 23° C., when 1 g of the polymer is weighed, subsequently immersed in 10 g of ion exchange water, and after having passed 24 hours, 0.5 g or more of the immersed polymer is dissolved in water. On the other hand, the "water-insoluble polymer" in the present Description refers to a polymer having a property that, under an environment of 1 atmosphere and 23° C., when 1 g of the polymer is weighed, subsequently immersed in 10 g of ion exchange water, and after having passed 24 hours, only less than 0.5 g of the immersed polymer is dissolved in water.

Examples of the water-soluble polymer having a coating film forming ability include mucopolysaccharides such as pullulan, hyaluronic acid, chondroitin sulfate, poly-γ-glutamic acid, modified cornstarch, β-glucan, glucooligosaccharide, heparin, and keratosulfate, natural macromolecules such as cellulose, pectin, xylan, lignin, glucomannan, galacturonic acid, psyllium seed gum, tamarind seed gum, gum arabic, gum tragacanth, water-soluble soybean polysaccharide, alginic acid, carrageenan, laminaran, agarose, fucoidan, methyl cellulose, hydroxypropyl cellulose, and hydroxypropyl methylcellulose, synthetic macromolecules such as a partially saponified polyvinyl alcohol (when not used in combination with a crosslinking agent), a low saponified polyvinyl alcohol, polyvinylpyrrolidone (PVP), polyethylene oxide, and sodium polyacrylate. These water-soluble polymers can be used singly or two or more can be used in combination. Of these water-soluble polymers, it is preferable to use pullulan, and synthetic macromolecules such as a partially saponified polyvinyl alcohol, a low saponified polyvinyl alcohol, polyvinylpyrrolidone, and polyethylene oxide from a viewpoint of easy production of a coating film. When polyethylene oxide is used as the water-soluble polymer, a number average molecular weight thereof is preferably 50,000 or more and 3,000,000 or less, and more preferably 100,000 or more and 2,500,000 or less.

Meanwhile, examples of the water-insoluble polymer having a coating film forming ability include a completely saponified polyvinyl alcohol insolubilizable after a coating film is formed, a partially saponified polyvinyl alcohol crosslinkable after a coating film is formed when used in combination with a crosslinking agent, oxazoline-modified silicones such as a poly(N-propanoylethyleneimine)graft-dimethylsiloxane/γ-aminopropylmethylsiloxane copolymer, a polyvinyl acetal diethylamino acetate, Zein (main component of corn protein), a polyester, a polylactic acid (PLA), an acrylic resin such as a polyacrylonitrile resin, and a polymethacrylic acid resin, and a polystyrene resin, a polyvinyl butyral resin, a polyethylene terephthalate resin, a polybutylene terephthalate resin, a polyurethane resin, a polyamide resin, a polyimide resin, and a polyamideimide resin. These water-insoluble polymers can be used singly or two or more can be used in combination. Of these water-insoluble polymers, it is preferable to use a completely saponified polyvinyl alcohol insolubilizable after a coating film is formed, a partially saponified polyvinyl alcohola crosslinkable after a coating film is formed when used in combination with a crosslinking agent, a polyvinyl butyral resin, a polyurethane resin, and oxazoline-modified silicones such as a poly(N-propanoylethyleneimine)graft-dimethylsiloxane/γ-aminopropylmethylsiloxane copolymer, a polyvinyl acetal diethylamino acetate, and Zein.

Component (a) is preferably a water-insoluble polymer having a coating film forming ability, and more preferably one or more selected from the group consisting of a partially saponified polyvinyl alcohol, a low saponified polyvinyl alcohol, a completely saponified polyvinyl alcohol, a polyvinyl butyral resin, a polyurethane resin, a polymethacrylic acid resin, an oxazoline-modified silicone, a polyvinyl acetal diethylamino acetate, and a polylactic acid.

A content of Component (a) in the composition for forming a coating film of the present invention is preferably 1.0 mass % or more, more preferably 2.0 mass % or more, further more preferably 4.0 mass % or more, further more preferably 6.0 mass % or more, and even more preferably 8.0 mass % or more. Additionally, it is preferably 35 mass % or less, more preferably 30 mass % or less, further more preferably 25 mass % or less, and even more preferably 20 mass % or less. A content of Component (a) in the composition for forming a coating film is preferably 1.0 mass % or more and 30 mass % or less, more preferably 2.0 mass % or more and 25 mass % or less, further more preferably 4.0 mass % or more and 20 mass % or less, and even more preferably 6.0 mass % or more and 20 mass % or less. Additionally, it is preferably 2.0 mass % or more and 35 mass % or less, more preferably 4.0 mass % or more and 30 mass % or less, further more preferably 6.0 mass % or more and 30 mass % or less, further more preferably 6.0 mass % or more and 25 mass % or less, further more preferably 8.0 mass % or more and 25 mass % or less, and even more preferably 8.0 mass % or more and 20 mass % or less. When Component (a) is contained in this proportion in the composition for forming a coating film, an intended coating film can be efficiently formed and a coating film composed of fibers can be formed stably.

The volatile substance as Component (b) is a substance having volatility in a liquid state. Component (b) in the composition for forming a coating film is blended for the purpose of finally forming a dry coating film, wherein the composition for forming a coating film placed within the electric field is sufficiently charged, subsequently discharged toward the skin from a nozzle tip, a charge density of the composition for forming a coating film becomes excess as Component (b) evaporates, and Component (b) further evaporates while broken down by Coulomb repulsion. For this purpose, the volatile substance has a vapor pressure at 20° C. of preferably 0.01 kPa or more and 106.66 kPa or less, more preferably 0.13 kPa or more and 66.66 kPa or less, further more preferably 0.67 kPa or more and 40.00 kPa or less, further more preferably 1.33 kPa or more and 40.00 kPa or less, and even more preferably 2.40 kPa or more and 40.00 kPa or less.

Of the volatile substances as Component (b), for example, monovalent chain fatty alcohols, monovalent cyclic fatty alcohols, and monovalent aromatic alcohols are preferably used as the alcohol. Examples of the monovalent chain fatty alcohol include straight chain or branched chain alcohols having 1 to 6 carbon atoms, examples of the monovalent cyclic fatty alcohol include cyclic fatty alcohols having 4 to 6 carbon atoms, and examples of the monovalent aromatic alcohol include benzyl alcohol and phenyl ethyl alcohol. Specific examples thereof include methanol, ethanol, isopropyl alcohol, n-propyl alcohol, n-butyl alcohol, 2-butyl alcohol, isobutyl alcohol, 2-methyl-2-propyl alcohol, n-pentanol, 2-pentanol, 3-pentanol, 2-methyl-1-butyl alcohol, 2-methyl-2-butyl alcohol, 3-methyl-1-butyl alcohol, 3-methyl-2-butyl alcohol, neopentyl alcohol, n-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, 2-ethyl-1-butanol, cyclobutanol, cyclopentanol, cyclohexanol, benzyl alcohol, and phenylethyl alcohol. These alcohols selected therefrom can be used singly or in combinations of two or more.

Of the volatile substances as Component (b), examples of the ketone include ketones having two alkyl groups having 1 to 4 carbon atoms such as acetone, methyl ethyl ketone, and methyl isobutyl ketone. These ketones can be used singly or two or more can be used in combination.

For the volatile substance as Component (b), one or more selected from the group consisting of the above alcohols and the above ketones can be used in combination.

The volatile substance as Component (b) is more preferably one or more selected from the group consisting of ethanol, isopropyl alcohol, and n-butyl alcohol, further more preferably one or more selected from the group consisting of ethanol and isopropyl alcohol, and even more preferably ethanol.

A content of Component (b) in the composition for forming a coating film is preferably 45 mass % or more, more preferably 50 mass % or more, further more preferably 55 mass % or more, and further more preferably 60 mass % or more. Additionally, it is preferably 98.8 mass % or less, more preferably 98 mass % or less, further more preferably 97 mass % or less, further more preferably 96 mass % or less, further more preferably 94 mass % or less, further more preferably 91 mass % or less, and even more preferably 88.5 mass % or less. A content of Component (b) in the composition for forming a coating film is preferably 50 mass % or more and 98.8 mass % or less, more preferably 50 mass % or more and 98 mass % or less, further more preferably 55 mass % or more and 96 mass % or less, and even more preferably 60 mass % or more and 94 mass % or less. Additionally, it is preferably 45 mass % or more and 97 mass % or less, more preferably 50 mass % or more and 94 mass % or less, further more preferably 50 mass % or more and 91 mass % or less, and even more preferably 50 mass % or more and 88.5 mass % or less. When Component (b) is contained in this proportion in the composition for forming a coating film, an intended coating film can be efficiently formed and a coating film composed of fibers can be formed stably. When Component (b) is contained in this proportion in the composition for forming a coating film, Component (b) can be efficiently and sufficiently volatilized from the composition for forming a coating film when carrying out the electrostatic spray method.

The plasticizer as Component (c) is a component which imparts flexibility to the coating film composed of fibers on the skin formed by an electrostatic spray, thereby enhancing the adhesion of the coating film to the skin and the scratch resistance, also enhancing the followability of the coating film along with the motion of the skin, and enhancing the skin compatibility of the coating film. Such a Component (c) is preferably a liquid oil agent at 20° C. Additionally, a feel modifier other than Component (c), Component (d), is a component which imparts, when used in combination with Component (c), flexibility to a coating film composed of fibers on the skin formed by an electrostatic spray and also enhances feels (e.g., smoothness, oily feeling, friction feeling, and stickiness) of the coating film.

For Component (c) and Component (d), suitable components are used depending on the property of the polymer having a coating film forming ability of Component (a).

The plasticizer as Component (c) is selected from those evaluated, based on the following evaluation criteria, as presenting a plasticizing ability to a water-insoluble polymer having a coating film forming ability of Component (a). The feel modifier other than Component (c) as Component (d) is selected from those evaluated, based on the following evaluation criteria, as presenting no plasticizing ability to a water-insoluble polymer having a coating film forming ability of Component (a).

(Evaluation Procedure)
(1) 8.8 g of an oil agent to be evaluated is added to a mighty vial No. 4 (manufactured by Maruemu Corporation).
(2) 1.2 g of a specific Component (a) a polymer having a coating film forming ability is added to the vial of (1), stirred using a spatula to thoroughly disperse the polymer in the oil agent, and the mighty vial is sealed. The polymer, when in a powder form, is used for the evaluation as it is. The polymer, when in a solution form, is caused to deposit by removing a solvent, cut to small pieces having 3 mm×3 mm×3 mm or less, and used for the evaluation. The polymer, when already in small pieces having 3 mm×3 mm×3 mm or less at the time of being deposited, is used for the evaluation as it is. The polymer, when in a film form, is cut to small pieces having 3 mm×3 mm×3 mm or less, and used for the evaluation.
(3) The vial of (2) was rotationally stirred for 1 week using a mix rotor (MVR-3R (manufactured by As One Corporation)) at a rotation speed of 100 r/min. (room temperature: 25° C.)
(4) The vial of (3) is allowed to stand at 25° C. for 2 hours and the state is visually observed.

(Evaluation Criteria)
Plasticizing ability presented: the polymer is completely dissolved in the oil agent (clear single-phase solution), or the polymer and the oil agent are mixed well and form a gel. However, when a part of the oil agent is separated (the polymer+oil agent phase, and the oil agent phase), the gel refers to the polymer+oil agent phase. (Shape of the polymer before evaluation is not maintained.)

No plasticizing ability presented: the polymer settles after the vial is allowed to stand and is dispersed again when the vial is shaken. The polymer settles again when the vial is further allowed to stand. The polymer is not dissolved or gelatinized. (Shape of the polymer before evaluation is maintained.)

Component (c) and Component (d) are not particularly limited as long as they are generally used in the field of cosmetic products but, for example, one or more selected from the group consisting of a polyol, a polyoxyalkylene glycol, a polyoxyalkylene alkyl ether, an ester oil, a silicone oil, a hydrocarbon oil, a liquid fat/oil, a solid fat/oil, a higher alcohol, and a nonionic surfactant can be used singly or two or more can be used in combination.

The polyol includes divalent to hexavalent polyols and examples thereof include polyols such as ethylene glycol, propylene glycol, 1,3-propanediol, glycerin, and 1,3-butylene glycol.

Examples of the polyoxyalkylene glycol include diethylene glycol, triethylene glycol, polyethylene glycol, dipropylene glycol, tripropylene glycol, polypropylene glycol, dibutylene glycol, tributylene glycol, polybutylene glycol, diglycerin, triglycerin, polyglycerin, polyoxyalkylene glycol (those containing as the constituent unit of the oxyalkylene one or more alkylene oxides such as ethylene oxide, propylene oxide, and butylene oxide), and mixtures thereof, polyoxyethylene glycerin, polyoxypropylene glyceryl ether, polyoxybutylene glyceryl ether, polyoxyalkylene glyceryl ether (those containing as the constituent unit of the oxyalkylene one or more alkylene oxides such as ethylene oxide, propylene oxide, and butylene oxide) and mixtures thereof. The polyoxyalkylene glycol herein is preferably those having an average molecular weight of 1,000 or less, and more preferably an average molecular weight of 600 or less.

Examples of the polyoxyalkylene alkyl ether include polyoxyethylene lauryl ether, polyoxyethylene oleyl ether, polyoxypropylene lauryl ether, polyoxypropylene oleyl ether, polyoxybutylene lauryl ether, polyoxybutylene oleyl ether, polyoxyalkylene alkyl ether (those containing as the constituent unit of the oxyalkylene one or more alkylene oxides such as ethylene oxide, propylene oxide, and butylene oxide, and an alkyl ether having an alkyl group having a straight chain or branched chain of about 1 to 20 carbon atoms), polyoxyethylene methyl glucoside, polyoxypropylene methyl glucoside, polyoxyalkylene methyl glucoside (those containing as the constituent unit of the oxyalkylene one or more alkylene oxides such as ethylene oxide, propylene oxide, and butylene oxide) and mixtures thereof.

Examples of the ester oil include fatty acid esters, e.g., octanoic acid esters such as cetyl octanoate, lauric acid esters such as hexyl laurate, myristic acid esters such as octyldodecyl myristate, palmitic acid esters such as octyl palmitate, stearic acid esters such as isocetyl stearate, isostearic acid esters such as isopropyl isostearate, isopalmitic acid esters such as octyl isopalmitate, oleic acid esters such as isodecyl oleate, adipic acid diesters such as diisopropyl adipate, sebacic acid diesters such as diethyl sebacate, malic acid diesters such as diisostearyl malate, isononanoic acid esters such as isononyl isononanoate and isotridecyl isononanoate, ethyl hexanoic acid esters such as cetyl ethylhexanoate, and neopentyl glycol diethylhexanoate, glycerides such as pentaerythrityl tetraethylhexanoate, triisostearin, glyceryl diisostearate, triethylhexanoin, (phytosteryl/behenyl) dimer dilinoleate, (phytosteryl/isostearyl/cetyl/stearyl/isostearl/cetyl/stearyl/behenyl) dimer dilinoleate, phytosteryl macadamiate, pentaerythrityl tetra(behenate/benzoate/ethylhexanoate), tripropylene glycol dipivalate, diisopropyl sebacate, isodecyl neopentanoate, hexyldecyl dimethyloctanoate, cetyl lactate, myristyl lactate, acetylated lanolin, cholesteryl 12-hydroxystearate, ethylene glycol di-2-ethyl hexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, glycerin trioctanoate, glycerin triisopalmitate, trimethylolpropane triisostearate, cetyl 2-ethylhexanoate, pentaerythritol tetra-2-ethylhexanoate, glycerin tri-2-ethylhexanoate, 2-ethylhexyl palmitate, glycerin trimyristate, glyceride tri-2-heptyl undecanoate, castor oil fatty acid methyl ester, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, di-2-hexyldecyl adipate, triethyl citrate, glycerin monofatty acid ester, glycerin difatty acid ester, and glycerin trifatty acid ester, acyl amino acid diesters such as di(phytosteryl/octyldodecyl) lauroyl glutamate, ultraviolet absorbers such as ethylhexyl methoxycinnamate, and alkyl benzoates.

Examples of the silicone oil include chained silicones such as dimethylpolysiloxane (dimethicone), methylphenyl polysiloxane, diphenyl polysiloxane (diphenyl dimethicone), diphenylsiloxy phenyl trimethicone, methylhydrogen polysiloxane, amodimethicone, aminoethylaminopropyl dimethicone, aminopropyl dimethicone, oxazoline-modified silicone, PEG-11 methyl ether dimethicone, PEG/PPG-20/22 butyl ether dimethicone, polyglyceryl-3 disiloxane dimethicone, polyglyceryl-3 disiloxane ethyl dimethicone, and lauryl polyglyceryl-3 disiloxane ethyl dimethicone, cyclic silicones such as cyclopentasiloxane methyl trimethicone, octamethylcyclotetrasiloxane, decamethylcyclopentasiloxane, and dodecamethylcyclohexasiloxane, silicone resins forming a three-dimensional network structure, and silicone rubbers.

Examples of the hydrocarbon oil include liquid paraffins, squalane, squalene, paraffins, isoparaffins, ceresin, isohexadecane, isododecane, ozokerite, pristane, paraffin waxes, vaselines, and microcrystalline waxes.

Examples of the liquid fat/oil include linseed oil, camellia oil, macadamia nut oil, corn oil, mink oil, olive oil, avocado oil, sasanqua oil, castor oil, safflower oil, rapeseed oil, soybean oil, peanut oil, triglycerin, glycerin trioctanoate, glycerin triisopalmitate, apricot kernel oil, cinnamon oil, jojoba oil, grapeseed_oil, sunflower oil, almond oil, sesame oil, wheat germ oil, rice germ oil, rice bran oil, cotton seed oil, tea oil, evening primrose oil, egg-yolk oil, beef foot oil, cod-liver oil, and pentaerythrit tetraoctanoate.

Examples of the solid fat/oil include cocoa butter, coconut oil, palm oil, palm kernel oil, beef tallow, suet, lard, horse fat, hydrogenated oil, hydrogenated castor oil, Japan wax, and shea butter.

Examples of the higher alcohol include saturated straight chain monovalent alcohols and unsaturated monovalent alcohols. Examples of the saturated straight chain monovalent alcohol include dodecanol (lauryl alcohol), tridodecanol, tetradodecanol (myristyl alcohol), pentadecanol, hexadecanol (cetyl alcohol), heptadecanol, octadecanol (stearyl alcohol), nonadecanol, icosanol (arachidyl alcohol), heneicosanol, docosanol (behenyl alcohol), tricosanol, tetracosanol (carnaubyl alcohol), pentacosanol, and hexacosanol (ceryl alcohol). Examples of the unsaturated monovalent alcohol include oleyl alcohol and elaidyl alcohol.

Examples of the nonionic surfactant include polyethylene glycol monofatty acid esters such as polyoxyethylene glycol monolaurate and polyoxyethylene glycol monostearate, polypropylene glycol monofatty acid esters such as polyoxypropylene glycol monolaurate and polyoxypropylene glycol monostearate, polybutylene glycol monofatty acid esters such as polyoxybutylene glycol monolaurate and polyoxybutylene glycol monostearate, polyoxyalkylene glycol monofatty acid esters (those containing as the constituent unit of the oxyalkylene one or more alkylene oxides such as ethylene oxide, propylene oxide and butylene oxide), and mixtures thereof, polyoxyalkylene glycol difatty acid esters (those containing as the constituent unit of the oxyalkylene one or more alkylene oxides such as ethylene oxide, propylene oxide and butylene oxide, and two fatty acids may be same kind or different kinds), and mixtures thereof, fatty acid polyoxyethylene sorbitans, maltitol hydroxy aliphatic alkyl ethers, alkylated polysaccharides, alkylglycosides, sucrose fatty acid esters, polyoxyethylene hydrogenated castor oil glyceryls, polyoxyethylene sorbit fatty acid esters, polyoxyethylene.polyoxypropylene block copolymers, tetrapolyoxyethylene.tetrapolyoxypropylene-ethylenediamine condensates, polyoxyethylene-beeswax.lanolin derivatives, alkanolamides, polyoxyethylene-propylene glycol fatty acid esters, polyoxyethylene-alkylamines, polyoxyethylene-fatty acid amides, alkylethoxydimethylamine oxides, trioleyl phosphates, and polyoxyethylene fatty acid glyceryls, and alkyl glyceryl ethers such as isostearyl glyceryl ether, isodecyl glyceryl ether and 2-ethylhexyl glyceryl ether.

When the polymer having a coating film forming ability as Component (a) is a polyvinyl butyral resin, preferable combinations of Component (c) and Component (d) are as follows.

The plasticizer as Component (c) is preferably a compound easily interactable with the hydroxy group, the ester, and the acetal moiety in the structure of the polyvinyl butyral resin, and examples specifically include polyols, polyoxyalkylene glycols (polyethers), polyoxyalkylene alkyl ethers, specific ester oils, specific silicone oils, and nonionic (non-ionic) surfactants but, from a viewpoint of enhancing the scratch resistance and a feel of a coating film, the plasticizer preferably contains a polyol, a polyoxyalkylene glycol, a glycerin monofatty acid ester, a glycerin difatty acid ester, a malic acid diester, an N-acyl amino acid ester, an ethylhexyl methoxycinnamate, or an alkyl benzoate. These compounds selected therefrom can be used singly or in combinations of two or more.

The polyol includes divalent to hexavalent polyol, and examples thereof include ethylene glycol, propylene glycol, 1,3-propanediol, glycerin, and 1,3-butylene glycol.

Examples of the polyoxyalkylene glycol include diethylene glycol, triethylene glycol, polyethylene glycol, dipropylene glycol, tripropylene glycol, polypropylene glycol, dibutylene glycol, tributylene glycol, polybutylene glycol, diglycerin, triglycerin, polyglycerin, polyoxyalkylene glycol (those containing as the constituent unit of the oxyalkylene one or more alkylene oxides such as ethylene oxide, propylene oxide, and butylene oxide), and mixtures thereof, polyoxyethylene glycerin, polyoxypropylene glyceryl ether, polyoxybutylene glyceryl ether, polyoxyalkylene glyceryl ether (those containing as the constituent unit of the oxyalkylene one or more alkylene oxides such as ethylene oxide, propylene oxide, and butylene oxide), and mixtures thereof.

Example of the polyoxyalkylene alkyl ether include polyoxyethylene lauryl ether, polyoxyethylene oleyl ether, polyoxypropylene lauryl ether, polyoxypropylene oleyl ether, polyoxybutylene lauryl ether, polyoxybutylene oleyl ether, polyoxyalkylene alkyl ether (those containing as the constituent unit of the oxyalkylene one or more alkylene oxides such as ethylene oxide, propylene oxide, and butylene oxide, and an alkyl ether having an alkyl group having a straight chain or branched chain of about 1 to 20 carbon atoms), polyoxyethylene methyl glucoside, polyoxypropylene methyl glucoside, polyoxyalkylene methyl glucoside (those containing as the constituent unit of the oxyalkylene one or more alkylene oxides such as ethylene oxide, propylene oxide, and butylene oxide), and mixtures thereof.

Examples of the specific ester oil include glycerin monofatty acid esters such as glyceryl monostearate, glyceryl monoisostearate, glyceryl monooleate, and glyceryl monopalmitate, glycerin difatty acid esters such as glyceryl distearate, glyceryl diisostearate, glyceryl dioleate, and glyceryl dipalmitate, lactic acid esters such as cetyl lactate and myristyl lactate, triethyl citrate, malic acid diesters such as diisostearyl malate, amino acid esters such as amino acid ester-2, acyl amino acid esters such as isopropyl lauroyl sarcosinate, ultraviolet absorbers such as ethylhexyl methoxycinnamate, and alkyl benzoates.

Examples of the specific silicone oil include amodimethicone, aminoethylaminopropyl dimethicone, aminopropyl dimethicone, oxazoline-modified silicone, PEG-11 methyl ether dimethicone, PEG/PPG-20/22 butyl ether dimethicone, polyglyceryl-3 disiloxane dimethicone, polyglyceryl-3 disiloxane ethyl dimethicone, and lauryl polyglyceryl-3 disiloxane ethyl dimethicone.

Examples of the nonionic surfactant include polyethylene glycol monofatty acid esters such as polyoxyethylene glycol monolaurate, and polyoxyethylene glycol monostearate, polypropylene glycol monofatty acid esters such as polyoxypropylene glycol monolaurate, and polyoxypropylene glycol monostearate, polybutylene glycol monofatty acid esters such as polyoxybutylene glycol monolaurate, and polyoxybutylene glycol monostearate, polyoxyalkylene glycol monofatty acid esters (those containing as the constituent unit of the oxyalkylene one or more alkylene oxides such as ethylene oxide, propylene oxide, and butylene oxide), and mixtures thereof, polyoxyalkylene glycol difatty acid esters (those containing as the constituent unit of the oxyalkylene one or more alkylene oxides such as ethylene oxide, propylene oxide, and butylene oxide, and two fatty acids may be same kind or different kinds), and mixtures thereof, fatty acid polyoxyethylene sorbitan, maltitol hydroxy aliphatic alkyl ether, alkylated polysaccharides, alkylglycosides, sucrose fatty acid esters, polyoxyethylene hydrogenated castor oil glyceryl, polyoxyethylene sorbit fatty acid esters, polyoxyethylene.polyoxypropylene block copolymers tetrapolyoxyethylene.tetrapolyoxypropylene-ethylenediamine condensates, polyoxyethylene-beeswax-lanolin derivatives, alkanolamides, polyoxyethylene-propylene glycol fatty acid esters, polyoxyethylene-alkylamines, polyoxyethylene-fatty acid amides, alkylethoxydimethylamine oxides, trioleyl phosphates, and polyoxyethylene fatty acid glyceryls. These plasticizers can be used singly or two or more can be used in combination.

When the polymer having a coating film forming ability as Component (a) is a polyvinyl butyral resin, Component (d) is preferably an oil agent with no polar functional group or few polar functional groups, and further more preferably an oil agent in which the number of hydroxy group is one or less in the structure. Specific examples of Component (d) include specific silicone oils, specific ester oils, hydrocarbon oils, liquid fats/oils, solid fats/oils, and higher alcohols but, from a viewpoint of enhancing the scratch resistance and a feel of a coating film, Component (d) preferably contains at least one selected from the group consisting of a silicone oil, a hydrocarbon oil, a palmitic acid ester, an isononanoic acid ester, neopentyl glycol diethylhexanoate, neopentyl glycol dicaprate, and an acyl amino acid diester, and, from a viewpoint of stabilizing environmental changes such as humidity and spinning performance in addition to the above viewpoints, preferably contains at least one selected from the group consisting of a silicone oil, a hydrocarbon oil, an isononanoic acid ester, neopentyl glycol diethylhexanoate, and neopentyl glycol dicaprate. These compounds selected therefrom can be used singly or in combinations of two or more, and more preferably two or more can be used in combination.

Examples of the specific silicone oil include chained silicones such as dimethylpolysiloxane (dimethicone), methylphenyl polysiloxane, diphenyl polysiloxane (diphenyl dimethicone), diphenylsiloxy phenyl trimethicone, and methylhydrogen polysiloxane, cyclic silicones such as cyclopentasiloxane methyl trimethicone, octamethylcyclotetrasiloxane, decamethylcyclopentasiloxane, and dodecamethylcyclohexasiloxane, silicone resins forming a three-dimensional network structure, and silicone rubbers.

Examples of the specific ester oil include fatty acid esters, e.g., octanoic acid esters such as cetyl octanoate, lauric acid esters such as hexyl laurate, myristic acid esters such as octyldodecyl myristate, palmitic acid esters such as octyl palmitate, stearic acid esters such as isocetyl stearate, isostearic acid esters such as isopropyl isostearate, isopalmitic acid esters such as octyl isopalmitate, oleic acid esters such as isodecyl oleate, adipic acid diesters such as diisopropyl adipate, sebacic acid diesters such as diethyl sebacate, malic acid diesters such as diisostearyl malate, isononanoic acid esters such as isononyl isononanoate, and isotridecyl isononanoate, ethyl hexanoic acid esters such as cetyl ethylhexanoate, f neopentyl glycol diethylhexanoate, glycerin trifatty acid esters such as pentaerythrityl tetraethylhexanoate, triisostearin, triethylhexanoin, phytosteryl macadamiate, pentaerythrityl tetra(behenate/benzoate/ethylhexanoate), tripropylene glycol dipivalate, diisopropyl sebacate, isodecyl neopentanoate, (phytosteryl/behenyl) dimer dilinoleate, (phytosteryl/isostearyl/cetyl/stearyl/isostearyl/cetyl/stearyl/behenyl) dimer dilinoleate, hexyldecyl dimethyloctanoate, acetylated lanolin, cholesteryl 12-hydroxystearate, dipentaerythritol fatty acid ester, N-alkyl glycol monoisostearate, neopentyl glycol dicaprate, diisostearyl malate, glycerin di-2-heptylundecanoate, glycerin trioctanoate, glycerin triisopalmitate, glycerin tri-2-ethylhexanoate, glycerin trimyristate, and glyceride tri-2-heptyl undecanoate, and acyl amino acid diesters such as ethylene glycol di-2-ethyl hexanoate, trimethylolpropane tri-2-ethylhexanoate, trimethylolpropane triisostearate, trimethylolpropane triisostearate, cetyl 2-ethylhexanoate, pentaerythritol tetra-2-ethylhexanoate, 2-ethylhexyl palmitate, castor oil fatty acid methyl ester, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, di-2-hexyldecyl adipate, and di(phytosteryl/octyldodecyl) lauroyl glutamate.

Examples of the hydrocarbon oil include liquid paraffins, squalane, squalene, paraffins, isoparaffins, ceresin, isohexadecane, isododecane, ozokerite, pristane, paraffin waxes, vaselines, and microcrystalline waxes.

Examples of the liquid fat/oil include linseed oil, camellia oil, macadamia nut oil, corn oil, mink oil, olive oil, avocado oil, sasanqua oil, castor oil, safflower oil, rapeseed oil, soybean oil, peanut oil, triglycerin, glycerin trioctanoate, glycerin triisopalmitate, apricot kernel oil, cinnamon oil, jojoba oil, grapeseed oil, sunflower oil, almond oil, sesame oil, wheat germ oil, rice germ oil, rice bran oil, cotton seed oil, tea oil, evening primrose oil, egg-yolk oil, beef foot oil, cod-liver oil, and pentaerythrite tetraoctanoate.

Examples of the solid fat/oil include cocoa butters, coconut oils, palm oils, palm kernel oils, beef tallows, suets, lards, horse fats, hydrogenated oils, hydrogenated castor oils, Japan waxes, and Shea butters.

Examples of the higher alcohol include saturated straight chain monovalent alcohols and unsaturated monovalent alcohols. Examples of the saturated straight chain monovalent alcohol include dodecanol (lauryl alcohol), tridodecanol, tetradodecanol (myristyl alcohol), pentadecanols, hexadecanol (cetyl alcohol), heptadecanol, octadecanol (stearyl alcohol), nonadecanol, icosanol (arachidyl alcohol), heneicosanol, docosanol (behenyl alcohol), tricosanol, tetracosanol (carnaubyl alcohol), pentacosanol, and hexacosanol (ceryl alcohol). Examples of the unsaturated monovalent alcohol include oleyl alcohol, and elaidyl alcohol.

A content of Component (c) in the composition for forming a coating film is preferably 0.10 mass % or more, more preferably 0.50 mass % or more, further more preferably 1.0 mass % or more, and even more preferably 1.5 mass % or more. Additionally, it is preferably 30 mass % or less, more preferably 25 mass % or less, further more preferably 20 mass % or less, and even more preferably 15 mass % or less. A content of Component (c) in the composition for forming a coating film is preferably 0.10 mass % or more and 30 mass % or less, more preferably 0.50 mass % or more and 25 mass % or less, further more preferably 1.0 mass % or more and 20 mass % or less, and even more preferably 1.0 mass % or more and 15 mass % or less. Additionally, it is preferably 0.50 mass % or more and 30 mass % or less, more preferably 1.0 mass % or more and 25 mass % or less, further more preferably 1.0 mass % or more and 20 mass % or less, and even more preferably 1.5 mass % or more and 15 mass % or less. When a content of Component (c) is within this range, flexibility is imparted to a coating film composed of fibers on the skin formed by an electrostatic spray, the adhesion of the coating film to the skin and scratch resistance are enhanced, the followability of the coating film along with the skin is enhanced, and the skin compatibility of the coating film is enhanced.

A content of Component (d) in the composition for forming a coating film is preferably 0.10 mass % or more, more preferably 0.50 mass % or more, further more preferably 1.0 mass % or more, and even more preferably 2.0 mass % or more. Additionally, it is preferably 40 mass % or less, more preferably 35 mass % or less, further more preferably 30 mass % or less, further more preferably 25 mass % or less, further more preferably 20 mass % or less, and even more preferably 15 mass % or less. A content of Component (d) in the composition for forming a coating film is preferably 0.10 mass % or more and 30 mass % or less, more preferably 0.50 mass % or more and 25 mass % or less, further more preferably 1.0 mass % or more and 20 mass % or less, and even more preferably 1.0 mass % or more and 15 mass % or less. Additionally, it is preferably 0.50 mass % or more and 40 mass % or less, more preferably 1.0 mass % or more and 35 mass % or less, further more preferably 2.0 mass % or more and 30 mass % or less, and even more preferably 2.0 mass % or more and 25 mass % or less. When a content of Component (d), when used in combination with Component (c), is within this range, flexibility is imparted to a coating film composed of fibers on the skin formed by an electrostatic spray and a feel of the coating film is enhanced.

A content mass ratio of Component (a) to Component (c) in the composition for forming a coating film, ((a)/(c)), is, from a viewpoint of the flexibility, the skin compatibility, the adhesion and the scratch resistance of the coating film composed of fibers formed by an electrostatic spray, preferably 0.033 or more, more preferably 0.10 or more, further more preferably 0.20 or more, further more preferably 0.40 or more, further more preferably 0.80 or more, further more preferably 1.0 or more, and even more preferably 1.5 or more. Additionally, it is preferably 300 or less, more preferably 60 or less, further more preferably 30 or less, further more preferably 20 or less, further more preferably 15 or less, further more preferably 10 or less, and even more preferably 8.0 or less. Such (a)/(c) is preferably 0.033 or more and 300 or less, more preferably 0.10 or more and 60 or less, further more preferably 0.20 or more and 30 or less, further more preferably 0.40 or more and 10 or less, and even more preferably 1.0 or more and 10 or less. Additionally, it is preferably 0.80 or more and 20 or less, more preferably 1.0 or more and 15 or less, further more preferably 1.0 or more and 10 or less, and even more preferably 1.5 or more and 8.0 or less.

A content mass ratio of Component (c) to Component (d) in the composition for forming a coating film, ((c)/(d)), is, from a viewpoint of the flexibility, the skin compatibility, the adhesion and the scratch resistance of the coating film composed of fibers formed by an electrostatic spray and further a viewpoint of enhancing a feel of the coating film, preferably 0.0033 or more, more preferably 0.030 or more, further more preferably 0.050 or more, further more preferably 0.10 or more, and even more preferably 0.50 or more. Additionally, it is preferably 300 or less, more preferably 60 or less, further more preferably 30 or less, further more preferably 10 or less, further more preferably 7.0 or less, further more preferably 5.0 or less, and even more preferably 3.5 or less. Such (c)/(d) is preferably 0.0033 or more and 300 or less, more preferably 0.030 or more and 60 or less, further more preferably 0.10 or more and 30 or less, and even more preferably 0.50 or more and 10 or less. Additionally, it is preferably 0.030 or more and 10 or less, more preferably 0.050 or more and 7.0 or less, further more preferably 0.10 or more and 5.0 or less, and even more preferably 0.10 or more and 3.5 or less.

A content mass ratio of Component (a) to Component (b) in the composition for forming a coating film, ((a)/(b)), is, from a viewpoint of efficiently forming an intended coating film, a viewpoint of stably forming a coating film composed of fibers, and a viewpoint of efficiently and sufficiently volatilizing Component (b) from the composition for forming a coating film when carrying out the electrostatic spray method, preferably 0.010 or more, more preferably 0.060 or more, further more preferably 0.080 or more, further more preferably 0.10 or more, further more preferably 0.11 or more, and even more preferably 0.12 or more. Additionally, it is preferably 0.60 or less, more preferably 0.45 or less, further more preferably 0.35 or less, further more preferably 0.33 or less, further more preferably 0.30 or more, further more preferably 0.25 or less, further more preferably 0.20 or less, and even more preferably 0.18 or less. Such (a)/(b) is preferably 0.010 or more and 0.60 or less, more preferably 0.060 or more and 0.33 or less, further more preferably 0.10 or more and 0.25 or less, further more preferably 0.11 or more and 0.20 or less, and even more preferably 0.12 or more and 0.18 or less. Additionally, it is preferably 0.060 or more and 0.45 or less, more preferably 0.080 or more and 0.35 or less, further more preferably 0.10 or more and 0.33 or less, further more preferably 0.11 or more and 0.30 or less, and even more preferably 0.12 or more and 0.25 or less.

A content mass ratio of Component (a) to Component (d) in the composition for forming a coating film, ((a)/(d)), is, from a viewpoint of enhancing a feel of a coating film composed of fibers formed by an electrostatic spray, preferably 0.033 or more, more preferably 0.10 or more, further more preferably 0.20 or more, further more preferably 0.40 or more, further more preferably 0.50 or more, and even more preferably 1.0 or more. Additionally, it is preferably 300 or less, more preferably 60 or less, further more preferably 30 or less, further more preferably 15 or less, further more preferably 10 or less, further more preferably 8.0 or less, and even more preferably 7.0 or less. Such (a)/(d) is preferably 0.033 or more and 300 or less, more preferably 0.10 or more and 60 or less, further more preferably 0.20 or more and 30 or less, further more preferably 0.40 or more and 10 or less, and even more preferably 1.0 or more and 10 or less. Additionally, it is preferably 0.10 or more and 15 or less, more preferably 0.20 or more and 10 or less, further more preferably 0.50 or more and 8.0 or less, and even more preferably 0.50 or more and 7.0 or less.

The composition for forming a coating film may contain, in addition to the above components, a conductivity controlling agent, an oil agent other than Components (c) and (d), a coloring pigment, an extender pigment, a dye, a fragrance, a repellent, an antioxidant, a stabilizer, a preservative, vitamins, and water. The conductivity controlling agent is, from a viewpoint of the conductivity enhancement, preferably an alkali metal salt or an ammonium salt, more preferably an ionic surfactant, and further more preferably one or more selected from the group consisting of a cationic surfactant and an anionic surfactant.

A content of the conductivity controlling agent in the composition for forming a coating film is not limited as long as an amount achieves the conductivity of the composition within the above ranges but, from a viewpoint of stably forming a coating film and a viewpoint of preventing a conductivity from excessively increasing, preferably 0.01 mass % or more and 10 mass % or less, more preferably 0.05 mass % or more, and further more preferably 0.1 mass % or more, and more preferably 8 mass % or less, further more preferably 6 mass % or less, further more preferably 2.5 mass % or less, and even more preferably 2 mass % or less.

A viscosity of the composition for forming a coating film at 25° C. is, from a viewpoint of stably forming a coating film composed of fibers on the skin and a viewpoint of spinning property when electrostatically spraying, drying of fibers, and thinning diameters of fibers, preferably 2 mPa·s or more, more preferably 5 mPa·s or more, further more preferably 10 mPa·s or more, further more preferably 30 mPa·s or more, further more preferably 50 mPa·s or more, and even more preferably 80 mPa·s or more. Additionally, it is preferably 3,000 mPa·s or less, more preferably 2,000 mPa·s or less, further more preferably 1,500 mPa·s or less, further more preferably 1,000 mPa·s or less, further more preferably 800 mPa·s or less, and even more preferably 500 mPa·s or less. A viscosity of the composition for forming a coating film ranges preferably 2 mPa·s or more and 3,000 mPa·s or less, more preferably 5 mPa·s or more and 2,000 mPa·s or less, further more preferably 10 mPa·s or more and 1,500 mPa·s or less, further more preferably 30 mPa·s or more and 1,000 mPa·s or less, further more preferably 50 mPa·s or more and 800 mPa·s or less, and even more preferably 80 mPa·s or more and 500 mPa·s or less. A viscosity of the composition for forming a coating film is measured using a B-type viscometer at 25° C. For the B-type viscometer, for example, a B-type viscometer (TVB-10M) manufactured by Toki Sangyo Co., Ltd. can be used. The measurement condition in such a case has a measurement temperature of 25° C. The measurement temperature herein refers to a temperature of the composition for forming a coating film. Type of a rotor and a rotation speed of the rotor are selected in accordance with specifications of a measurement apparatus to be used depending on a viscosity of the composition for forming a coating composition. For example, when the above B-type viscometer (TVB-10M) manufactured by Toki Sangyo Co., Ltd. is used, the measurement can be achieved using an M2 rotor at 6 rpm when a viscosity of the composition for a coating film is 2,500 mPa·s or more, an M2 rotor at 12 rpm when such a viscosity is 1,000 mPa·s or more and less than 2,500 mPa·s, an M2 rotor at 30 rpm when such a viscosity is 500 mPa·s or more and less than 1,000 mPa·s, an M2 rotor at 60 rpm when such a viscosity is 100 mPa·s or more and less than 500 mPa·s, and an M1 rotor at 60 rpm when such a viscosity is less than 100 mPa·s. Additionally, instructions for use of the above B-type viscometer (TVB-10M) manufactured by Toki Sangyo Co., Ltd. also include measurement conditions other than the above measurement conditions and a viscosity can also be measured under other measurement conditions depending on a viscosity of the composition for forming a coating film.

Subsequently described is a method for forming a coating film composed of fibers directly formed on the skin by an electrostatic spray using the composition for forming a coating film of the present invention.

The composition for forming a coating film is sprayed directly to a site at which a coating film is intended to be formed on the human skin by the electrostatic spray method. The electrostatic spray method contains a step for electrostatically spraying the composition for forming a coating film to the skin using an electrostatic spray apparatus. The electrostatic spray apparatus basically has a container for accommodating the above composition, a nozzle for discharging the composition, a feed apparatus for feeding the composition accommodated in the container to the nozzle, and a power supply for applying a voltage to the nozzle.

FIG. 1 is a diagram showing a structure of the electrostatic spray apparatus preferably used in the present invention. An electrostatic spray apparatus 10 shown in the same figure is equipped with a low-voltage power supply 11. The low-voltage power supply 11 is for generating several volts to ten and some volts. The low-voltage power supply 11 is preferably composed of one or more batteries for the purpose of increasing the portability of the electrostatic spray apparatus 10. Additionally, batteries, when used as the low-voltage power supply 11, can be easily replaceable as needed, hence advantageous. Instead of batteries, an AC adapter can also be used as the low-voltage power supply 11.

The electrostatic spray apparatus 10 is also equipped with a high-voltage power supply 12. The high-voltage power supply 12 is connected to the low-voltage power supply 11 and equipped with an electric circuit (not shown) to boost the voltage generated at the low-voltage power supply 11 to a high voltage. A voltage boost electric circuit is generally made up of a transformer, a capacitor, and a semiconductor element.

The electrostatic spray apparatus 10 is further equipped with an auxiliary electric circuit 13. The auxiliary electric circuit 13 is interposed between the low-voltage power supply 11 and the high-voltage power supply 12 described above and functions to adjust a voltage of the low-voltage power supply 11 thereby allowing the high-voltage power supply 12 to operate stably. The auxiliary electric circuit 13 has a function of controlling the rotation speed of a motor equipped by a micro gear pump 14 to be described later. Controlling the rotation speed of the motor controls a feed amount of the composition for forming a coating film to the micro gear pump 14 from a container 15 for the composition for forming a coating film. A switch SW is attached between the auxiliary electric circuit 13 and the low-voltage power supply 11 and the electrostatic spray apparatus 10 can start/stop by switching ON-OFF the switch SW.

The electrostatic spray apparatus 10 is further equipped with a nozzle 16. The nozzle 16 is composed of various conductors such as a metal to begin with and non-conductors such as plastic, rubber, and ceramic, and has a shape which can discharge the composition for forming a coating film from the tip thereof. Inside the nozzle 16, a microspace through which the composition for forming a coating film passes is formed longitudinally along with the nozzle 16. A cross-sectional size of this microspace is preferably 100 μm or more and 1,000 μm or less when expressed in the diameter.

The nozzle 16 communicates with the micro gear pump 14 via a pipeline 17. The pipeline 17 may be a conductor or a non-conductor. Additionally, the nozzle 16 is electrically connected to the high-voltage power supply 12. This enables the application of a high-voltage to the nozzle 16. In this case, the nozzle 16 and the high-voltage power supply 12 are electrically connected via an electric current limiting resistor 19 to prevent an excess electric current from flowing when a human body directly touches the nozzle 16.

The micro gear pump 14 communicating with the nozzle 16 via the pipeline 17 functions as a feed apparatus for feeding the composition for forming a coating film accommodated in the container 15 to the nozzle 16. The micro gear pump 14 receives a feed of power supply from the low-voltage power supply 11 and operates. The micro gear pump 14 is configured in such a way as to feed a predetermined amount of the composition for forming a coating film to the nozzle 16 in response to the control by the auxiliary electric circuit 13.

The container 15 is connected to the micro gear pump 14 via a flexible pipeline 18. In the container 15, the composition for forming a coating film is accommodated. The container 15 is preferably an exchangeable cartridge type.

Figure 2:
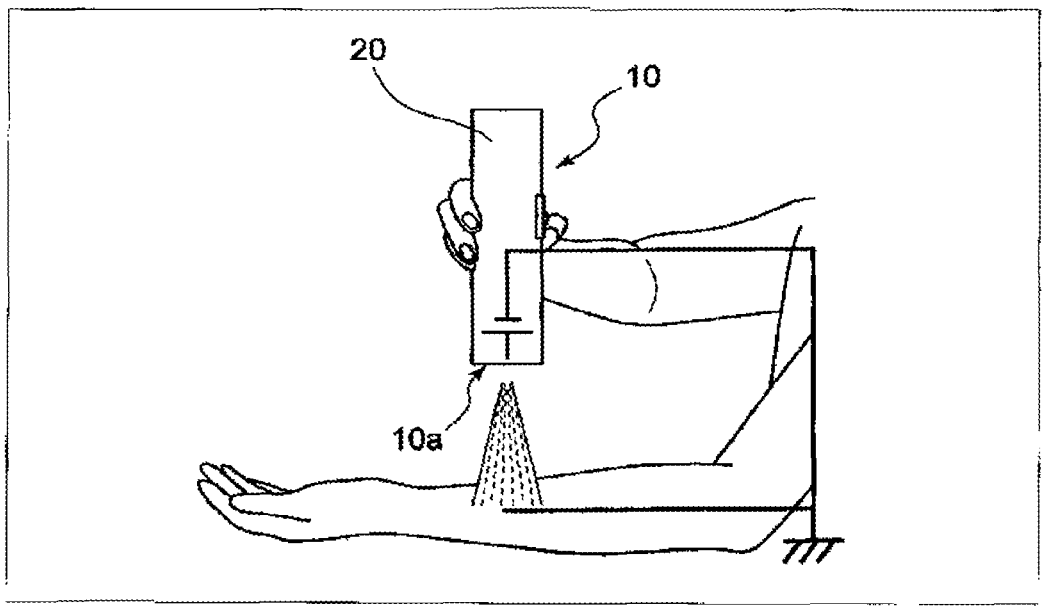
FIG. 2 illustrates a schematic view showing a fashion for carrying out an electrostatic spray method using the electrostatic spray apparatus.

The electrostatic spray apparatus 10 having the above structure can be used as shown in, for example, FIG. 2. FIG. 2 shows a hand-held electrostatic spray apparatus 10 having a size holdable by one hand. The electrostatic spray apparatus 10 shown in the same figure accommodates all the members of the structural diagram shown in FIG. 1 inside a cylindrical housing 20. The nozzle (not shown) is arranged at an end 10a of a longitudinal direction of the housing 20. The nozzle is arranged in the housing 20 with a coming-out direction of the composition in line with the longitudinal direction of the housing 20 so that it protrudes toward the skin side. When the nozzle tip is arranged in such a way as to protrude toward the skin along with the longitudinal direction of the housing 20, the composition for forming a coating film is less likely to attach to the housing thereby stably forming a coating film.

When operating the electrostatic spray apparatus 10, a user, that is, a person who forms a coating film on a site at which the coating film is formed on the skin by an electrostatic spray, holds the apparatus 10 with a hand and turns the end 10a of the apparatus 10 at which the nozzle (not shown) is arranged toward an application site to which an electrostatic spray is carried out. FIG. 2 shows a state in which an end 10a of the electrostatic spray apparatus 10 is turned toward the inner side of the user's forearm. In this state, the apparatus 10 is switched ON to carry out the electrostatic spray method. When the apparatus 10 is turned on, an electric field is generated between the nozzle and the skin. In the embodiment shown in FIG. 2, a positive high voltage is applied to the nozzle thereby making the skin a negative electrode. When the electric field is generated between the nozzle and the skin, the composition for forming a coating film at the nozzle tip section is polarized due to electrostatic induction and forms a corn shape at the tip part, and droplets of the charged composition for forming a coating film is discharged into the air from the corn tip toward the skin along with the electric field. As Component (b), a solvent, evaporates from the charged composition for forming a coating film discharged into the air, the composition for forming a coating film has an excessed charge density on the surface, proceeds in the air by Coulomb repulsion while repeatedly broken down, and reaches the skin. In this instance, when a viscosity of the composition for forming a coating film is suitably adjusted, the volatile substance, a solvent, is caused to volatilize from droplets while the composition is discharged into the air, and the polymer having a coating film forming ability, a solute, of Component (a) forms fibers as elongated by a potential difference while solidified, whereby the formed fibers are caused to deposit at an application site. For example, when a viscosity of the composition for forming a coating film is increased, the composition is likely to deposit at an application site in the form of fibers. Herewith, a porous coating film composed of fibrous deposits is formed on the surface of an application site. Such a porous coating film composed of fibrous deposits can also be formed by adjusting the distance between the nozzle and the skin or a voltage to be applied to the nozzle.

A high potential difference is being generated between the nozzle and the skin while carrying out the electrostatic spray method. However, the impedance is so significant that an electric current flowing through the human body is extremely small. For example, the present inventors confirmed that, for example, an electric current flowing through the human body while carrying out the electrostatic spray method is some digits smaller than an electric current flowing through the human body by static electricity generated in daily life.

When fibrous deposits are formed by the electrostatic spray method, a thickness of fibers when expressed by a diameter equivalent to a circle is preferably 10 nm or more, and more preferably 50 nm or more. Additionally, it is preferably 3,000 nm or less, more preferably 1,000 nm or less, and further more preferably 800 nm or less. The thickness of a fiber can be measured by, for example, magnifying the fibers 10,000 times to observe using a scanning electron microscopic (SEM), excluding defects (fiber masses, fiber overlaps, and droplets) from the two-dimensional images, randomly selecting 10 fibers, drawing a line perpendicular to the longitudinal direction of the fibers, and directly reading a diameter of the fibers. The fiber of the present invention is preferably a continuous fiber and preferably has a length of at least 100 times or more a thickness of the fiber. For examples, a formed coating film preferably contains fibers containing Component (a) and having a length of preferably 10 μm or more, more preferably 50 μm or more, and further more preferably 100 μm or more. In the present Description, a fiber having a length of 100 times or more a thickness of the fiber is defined as the "continuous fiber." The cross-sectional shape of the fiber is preferably circle or oval, and the fiber thickness refers to the diameter in the case of circle and a length of the major axis in the case of oval. The coating film produced by the electrostatic spray method is preferably porous non-continuous coating film composed of one or more continuous fibrous deposits.

According to the electrostatic spray method, the composition for forming a coating film is charged and sprayed and affected by the moisture in the air when a humidity is high but can be less likely affected when a conductivity controlling agent is contained.

In the method for producing the composition for forming a coating film, one may stir a mixed solution containing all components but it is preferable to have Step 1 for stirring Mixed solution 1 containing the components other than Component (a) and subsequently Step 2 for adding Component (a) followed by stirring and mixing. These Step 1 and Step 2 are preferably carried out at normal temperature of 10° C. to 30° C.

A distance between the nozzle and the skin is, depending on a voltage to be applied to the nozzle through, preferably 10 mm or more, more preferably 20 mm or more, and further more preferably 40 mm or more. Additionally, it is preferably 160 mm or less, more preferably 140 mm or less, and further more preferably 120 mm or less. A distance between the nozzle and the skin within this range can enhance the formability of a coating film. A distance between the nozzle and the skin can be measured by a commonly used non-contact sensor.

A basis weight of the coating film is, regardless of the coating film formed by the electrostatic spray method being porous or not, preferably 0.10 g/m$^2$ or more, and more preferably 1.0 g/m$^2$ or more. Additionally, it is preferably 50 g/m$^2$ or less, and more preferably 40 g/m$^2$ or less. A basis weight of the formed coating film is preferably 0.10 g/m$^2$ or more and 50 g/m$^2$ or less, and more preferably 1.0 g/m$^2$ or more and 40 g/m$^2$ or less. When a basis weight of the coating film is set as such, the skin compatibility, adhesion, and scratch resistance of the coating film can be compatible.

In the present invention, a skincare cosmetic may be applied to the skin before or after the electrostatic spray step for forming a coating film on the skin by an electrostatic spray using the composition for forming a coating film of the present invention described above. It is particularly preferable to form the coating film by an electrostatic spray using the composition for forming a coating film of the present invention after a skincare cosmetic is applied to the skin. Thus, when an electrostatic spray is carried out after the application of a skincare cosmetic, the skincare cosmetic present on the skin can be covered with the coating film thereby notably enhancing the compatibility of the skincare cosmetic with the skin and stably retaining the skincare cosmetic on the skin for a long period of time.

The skincare cosmetic used herein includes skin lotions, milky lotions, creams, serums (whitening, anti-wrinkle, etc.), all-in-one cosmetics, UV care cosmetics, BB creams, oils, oil gels, and lotions.

Examples of the application means of the above skincare cosmetics to the skin other than the electrostatic spray include application by hands and/or fingers, application using a nonwoven cloth such as cotton, spraying using a usual spray, spraying mist, steaming, dripping, and sprinkling.

In reference with the embodiments described above, the present invention further discloses the following compositions and methods.

<1> A composition for forming a coating film, for forming a coating film composed of fibers directly on the skin by an electrostatic spray, the composition comprising the following Components (a), (b), (c), and (d):
(a) a polymer having a coating film forming ability
(b) one or more volatile substances selected from the group consisting of an alcohol and a ketone
(c) a plasticizer
(d) a feel modifier other than Component (c).

<2> The composition for forming a coating film according to <1>, wherein Component (a) is a water-insoluble polymer having a coating film forming ability, and preferably one or more selected from the group consisting of a completely saponified polyvinyl alcohol insolubilizable after forming a coating film, a partially saponified polyvinyl alcohol crosslinkable after forming a coating film when used in combination with a crosslinking agent, an oxazoline-modified silicone such as poly(N-propanoyl-ethyleneimine)graft-dimethylsiloxane/γ-aminopropylmethylsiloxane copolymer, a polyvinyl acetal diethylamino acetate, Zein (main component of corn protein), a polyester, a polylactic acid (PLA), an acrylic resin such as a polyacrylonitrile resin, and a polymethacrylic acid resin, and a polystyrene resin, a polyvinyl butyral resin, a polyethylene terephthalate resin, a polybutylene terephthalate resin, a polyurethane resin, a polyamide resin, a polyimide resin, and a polyamideimide resin, and further more preferably one or more selected from the group consisting of a completely saponified polyvinyl alcohol insolubilizable after forming a coating film, a partially saponified polyvinyl alcohol crosslinkable after forming a coating film when used in combination with a crosslinking agent, a polyvinyl butyral resin, a polyurethane resin, an oxazoline-modified silicone, a polyvinyl acetal diethylamino acetate, and Zein.

<3> The composition for forming a coating film according to <1> or <2>, wherein a content of Component (a) is preferably 1.0 mass % or more, more preferably 2.0 mass % or more, further more preferably 4.0 mass % or more, further more preferably 6.0 mass % or more, and even more preferably 8.0 mass % or more, and preferably 35 mass % or less, more preferably 30 mass % or less, further more preferably 25 mass % or less, and even more preferably 20 mass % or less, and preferably 1.0 mass % or more and 30 mass % or less, more preferably 2.0 mass % or more and 25 mass % or less, further more preferably 4.0 mass % or more and 20 mass % or less, further more preferably 6.0 mass % or more and 20 mass % or less, and preferably 2.0 mass % or more and 35 mass % or less, more preferably 4.0 mass % or more and 30 mass % or less, further more preferably 6.0 mass % or more and 30 mass % or less, further more preferably 6.0 mass % or more and 25 mass % or less, further more preferably 8.0 mass % or more and 25 mass % or less, and even more preferably 8.0 mass % or more and 20 mass % or less.

<4> The composition for forming a coating film according to any one of <1> to <3>, wherein a content of Component (a) is 2.0 mass % or more and 25 mass % or less.

<5> The composition for forming a coating film according to any one of <1> to <3>, wherein a content of Component (a) is 6.0 mass % or more and 30 mass % or less.

<6> The composition for forming a coating film according to any one of <1> to <5>, wherein Component (b) has a vapor pressure at 20° C. of preferably 0.01 kPa or more and 106.66 kPa or less, more preferably 0.13 kPa or more and 66.66 kPa or less, further more preferably 0.67 kPa or more and 40.00 kPa or less, further more preferably 1.33 kPa or more and 40.00 kPa or less, and even more preferably 2.40 kPa or more and 40.00 kPa or less.

<7> The composition for forming a coating film according to any one of <1> to <6>, wherein the alcohol of Component (b) is preferably one or more selected from the group consisting of a monovalent chain fatty alcohol, a monovalent cyclic fatty acid, and a monovalent aromatic alcohol, preferably one or more selected from the group consisting of a straight chain or branched chain monovalent chain fatty alcohol having 1 to 6 carbon atoms, a monovalent cyclic fatty alcohol having 4 to 6 carbon atoms, benzyl alcohol, and phenyl ethyl alcohol, further more preferably one or more selected from the group consisting of ethanol, isopropyl alcohol, n-butyl alcohol, phenyl ethyl alcohol, n-propanol, and n-pentanol.

<8> The composition for forming a coating film according to any one of <1> to <7>, wherein the ketone of Component (b) is preferably a ketone having two alkyl groups having 1 to 4 carbon atoms, and further more preferably one or more selected from the group consisting of acetone, methyl ethyl ketone, and methyl isobutyl ketone.

<9> The composition for forming a coating film according to any one of <1> to <8>, wherein Component (b) is preferably one or more selected from the group consisting of ethanol, isopropyl alcohol, and n-butyl alcohol, more preferably one or more selected from the group consisting of ethanol and isopropyl alcohol, and further more preferably ethanol.

<10> The composition for forming a coating film according to any one of <1> to <9>, wherein a content of Component (b) is preferably 45 mass % or more, more preferably 50 mass % or more, further more preferably 55 mass % or more, and further more preferably 60 mass % or more, and preferably 98.8 mass % or less, more preferably 98 mass % or less, further more preferably 97 mass % or less, further more preferably 96 mass % or less, further more preferably 94 mass % or less, further more preferably 91 mass % or less, and even more preferably 88.5 mass % or less, and preferably 50 mass % or more and 98.8 mass % or less, more preferably 50 mass % or more and 98 mass % or less, further more preferably 55 mass % or more and 96 mass % or less, further more preferably 60 mass % or more and 94 mass % or less, and preferably 45 mass % or more and 97 mass % or less, more preferably 50 mass % or more and 94 mass % or less, further more preferably 50 mass % or more and 91 mass % or less, and even more preferably 50 mass % or more and 88.5 mass % or less.

<11> The composition for forming a coating film according to any one of <1> to <10>, wherein a content of Component (b) is 50 mass % or more and 98 mass % or less.

<12> The composition for forming a coating film according to any one of <1> to <10>, wherein a content of Component (b) is 50 mass % or more and 91 mass % or less.

<13> The composition for forming a coating film according to any one of <1> to <12>, wherein Component (c) and Component (d) are one or more selected from the group consisting of a polyol, a polyoxyalkylene glycol, a polyoxyalkylene alkyl ether, an ester oil, a silicone oil, a hydrocarbon oil, a liquid fat/oil, a solid fat/oil, a higher alcohol, and a nonionic surfactant.

<14> The composition for forming a coating film according to any one of <1> to <13>, wherein Component (c) is a compound easily interactable with the hydroxy, ester or acetal moiety in the structure of the polyvinyl butyral resin, preferably one or more selected from the group consisting of a polyol, a polyoxyalkylene glycol, a polyoxyalkylene alkyl ether, a specific ester oil, a specific silicone oil, and a nonionic surfactant, and more preferably one or more selected from the group consisting of a polyol, a polyoxyalkylene glycol, a glycerin monofatty acid ester, a glycerin difatty acid ester, a malic acid diester, an N-acyl amino acid ester, ethylhexyl methoxycinnamate, and an alkyl benzoate.

<15> The composition for forming a coating film according to any one of <1> to <14>, wherein a content of Component (c) is preferably 0.10 mass % or more, more preferably 0.50 mass % or more, further more preferably 1.0 mass % or more, and further more preferably 1.5 mass % or more, and preferably 30 mass % or less, more preferably 25 mass % or less, further more preferably 20 mass % or less, further more preferably 15 mass % or less, and preferably 0.10 mass % or more and 30 mass % or less, more preferably 0.50 mass % or more and 25 mass % or less, further more preferably 1.0 mass % or more and 20 mass % or less, and further more preferably 1.0 mass % or more and 15 mass % or less, and preferably 0.50 mass % or more and 30 mass % or less, more preferably 1.0 mass % or more and 25 mass % or less, further more preferably 1.0 mass % or more and 20 mass % or less, and even more preferably 1.5 mass % or more and 15 mass % or less.

<16> The composition for forming a coating film according to any one of <1> to <15>, wherein a content of Component (c) is 0.50 mass % or more and 25 mass % or less.

<17> The composition for forming a coating film according to any one of <1> to <15>, wherein a content of Component (c) is 1.0 mass % or more and 20 mass % or less.

<18> The composition for forming a coating film according to any one of <1> to <17>, wherein Component (d) is an oil agent with no polar functional group or few polar functional groups, preferably an oil agent in which the number of hydroxy group is one or less in the structure, more preferably one or more selected from the group consisting of a specific silicone oil, a specific ester oil, a hydrocarbon oil, and an alkyl ether oil, further more preferably one or more selected from the group consisting of a specific silicone oil, a specific ester oil, and a hydrocarbon oil, further more preferably one or more selected from the group consisting of a silicone oil, a hydrocarbon oil, a palmitic acid ester, an isononanoic acid ester, neopentyl glycol diethylhexanoate, neopentyl glycol dicaprate, and an acyl amino acid diester, further more preferably one or more selected from the group consisting of a silicone oil, a hydrocarbon oil, an isononanoic acid ester, neopentyl glycol diethylhexanoate, and neopentyl glycol dicaprate.

<19> The composition for forming a coating film according to any one of <1> to <18>, wherein a content of Component (d) is preferably 0.10 mass % or more, more preferably 0.50 mass % or more, further more preferably 1.0 mass % or more, and further more preferably 2.0 mass % or more, and preferably 40 mass % or less, more preferably 35 mass % or less, further more preferably 30 mass % or less, further more preferably 25 mass % or less, further more preferably 20 mass % or less, further more preferably 15 mass % or less, and preferably 0.10 mass % or more and 30 mass % or less, more preferably 0.50 mass % or more and 25 mass % or less, further more preferably 1.0 mass % or more and 20 mass % or less, and even more preferably 1.0 mass % or more and 15 mass % or less, and preferably 0.50 mass % or more and 40 mass % or less, more preferably 1.0 mass % or more and 35 mass % or less, further more preferably 2.0 mass % or more and 30 mass % or less, and even more preferably 2.0 mass % or more and 25 mass % or less.

<20> The composition for forming a coating film according to any one of <1> to <19>, wherein a content of Component (d) is 0.50 mass % or more and 25 mass % or less.

<21> The composition for forming a coating film according to any one of <1> to <19>, wherein a content of Component (d) is 2.0 mass % or more and 30 mass % or less.

<22> The composition for forming a coating film according to any one of <1> to <21>, wherein a content mass ratio of Component (a) to Component (c), ((a)/(c)), is preferably 0.033 or more, more preferably 0.10 or more, further more preferably 0.20 or more, further more preferably 0.40 or more, further more preferably 0.80 or more, further more preferably 1.0 or more, and even more preferably 1.5 or more, and preferably 300 or less, more preferably 60 or less, further more preferably 30 or less, further more preferably 20 or less, further more preferably 15 or less, further more preferably 10 or less, and even more preferably 8.0 or less, and preferably 0.033 or more and 300 or less, more preferably 0.10 or more and 60 or less, further more preferably 0.20 or more and 30 or less, further more preferably 0.40 or more and 10 or less, and even more preferably 1.0 or more and 10 or less, and preferably 0.80 or more and 20 or less, more preferably 1.0 or more and 15 or less, further more preferably 1.0 or more and 10 or less, and even more preferably 1.5 or more and 8.0 or less.

<23> The composition for forming a coating film according to any one of <1> to <22>, wherein a content mass ratio of Component (a) to Component (c), ((a)/(c)), is 0.2 or more and 30 or less.

<24> The composition for forming a coating film according to any one of <1> to <22>, wherein a content mass ratio of Component (a) to Component (c), ((a)/(c)), is 1.0 or more and 10 or less.

<25> The composition for forming a coating film according to any one of <1> to <24>, wherein a content mass ratio of Component (c) to Component (d), ((c)/(d)), is preferably 0.0033 or more, more preferably 0.030 or more, further more preferably 0.050 or more, further more preferably 0.10 or more, further more preferably 0.50 or more, and preferably 300 or less, more preferably 60 or less, further more preferably 30 or less, further more preferably 10 or less, further more preferably 7.0 or less, further more preferably 5.0 or less, and even more preferably 3.5 or less, and preferably 0.0033 or more and 300 or less, more preferably 0.030 or more and 60 or less, further more preferably 0.10 or more and 30 or less, and even more preferably 0.50 or more and 10 or less, and preferably 0.030 or more and 10 or less, more preferably 0.050 or more and 7.0 or less, further more preferably 0.10 or more and 5.0 or less, and even more preferably 0.10 or more and 3.5 or less.

<26> The composition for forming a coating film according to any one of <1> to <25>, wherein a content mass ratio of Component (c) to Component (d), ((c)/(d)), is 0.10 or more and 30 or less.

<27> The composition for forming a coating film according to any one of <1> to <25>, wherein a content mass ratio of Component (c) to Component (d), ((c)/(d)), is 0.10 or more and 5.0 or less.

<28> The composition for forming a coating film according to any one of <1> to <27>, wherein a content mass ratio of Component (a) to Component (b), ((a)/(b)), is preferably 0.010 or more, more preferably 0.060 or more, further more preferably 0.080 or more, further more preferably 0.10 or more, further more preferably 0.11 or more, further more preferably 0.12 or more, and preferably 0.60 or less, more preferably 0.45 or less, further more preferably 0.35 or less, further more preferably 0.33 or less, further more preferably 0.30 or less, further more preferably 0.25 or less, further more preferably 0.20 or less, and even more preferably 0.18 or less, and preferably 0.010 or more and 0.60 or less, more preferably 0.060 or more and 0.33 or less, further more preferably 0.10 or more and 0.25 or less, further more preferably 0.11 or more and 0.20 or less, further more preferably 0.12 or more and 0.18 or less, and preferably 0.060 or more and 0.45 or less, more preferably 0.080 or more and 0.35 or less, further more preferably 0.10 or more and 0.33 or less, further more preferably 0.11 or more and 0.30 or less, and much preferably 0.12 or more and 0.25 or less.

<29> The composition for forming a coating film according to any one of <1> to <28>, wherein a content mass ratio of Component (a) to Component (b), ((a)/(b)), is 0.10 or more and 0.25 or less.

<30> The composition for forming a coating film according to any one of <1> to <28>, wherein a content mass ratio of Component (a) to Component (b), ((a)/(b)), is 0.11 or more and 0.30 or less.

<31> The composition for forming a coating film according to any one of <1> to <30>, wherein a content mass ratio of Component (a) to Component (d), ((a)/(d)), is preferably 0.033 or more, more preferably 0.10 or more, further more preferably 0.20 or more, further more preferably 0.40 or more, further more preferably 0.50 or more, and even more preferably 1.0 or more, and preferably 300 or less, more preferably 60 or less, further more preferably 30 or less, further more preferably 15 or less, further more preferably 10 or less, further more preferably 8.0 or less, and even more preferably 7.0 or less, and preferably 0.033 or more and 300 or less, more preferably 0.10 or more and 60 or less, further more preferably 0.20 or more and 30 or less, further more preferably 0.40 or more and 10 or less, further more preferably 1.0 or more and 10 or less, further more preferably 0.10 or more and 15 or less, further more preferably 0.20 or more and 10 or less, further more preferably 0.50 or more and 8.0 or less, and even more preferably 0.50 or more and 7.0 or less.

<32> The composition for forming a coating film according to any one of <1> to <31>, wherein a content mass ratio of Component (a) to Component (d), ((a)/(d)), is 0.20 or more and 30 or less.

<33> The composition for forming a coating film according to any one of <1> to <31>, wherein a content mass ratio of Component (a) to Component (d), ((a)/(d)), is 0.5 or more and 8.0 or less.

<34> The composition for forming a coating film according to any one of <1> to <33> comprising components selected from the group consisting of a conductivity controlling agent, an oil agent other than Components (c) and (d), a coloring pigment, an extender pigment, a dye, a fragrance, a repellent, an antioxidant, a stabilizer, a preservative, a vitamin, and water.

<35> The composition for forming a coating film according to <34>, wherein the conductivity controlling agent is preferably a component achieving a conductivity of the composition for forming a coating film at 25° C. of 10 µS/cm or more and 300 µS/cm or less.

<36> The composition for forming a coating film according to <34> or <35>, wherein the conductivity controlling agent is preferably an alkali metal salt or an ammonium salt, more preferably an ionic surfactant, and further more preferably one or more selected from the group consisting of a cationic surfactant and an anionic surfactant.

<37> The composition for forming a coating film according to any one of <34> to <36>, wherein the conductivity controlling agent is one or more selected from the group consisting of a quaternary ammonium salt and an acyl amino acid salt.

<38> The composition for forming a coating film according to any one of <34> to <37>, wherein a content of the conductivity controlling agent is 0.010 mass % or more, more preferably 0.050 mass % or more, and further more preferably 0.10 mass % or more, and preferably 10 mass % or less, more preferably 8.0 mass % or less, further more preferably 6.0 mass % or less, further more preferably 2.5 mass % or less, and even more preferably 2.0 mass % or less, and preferably 0.010 mass % or more and 10 mass % or less, more preferably 0.050 mass % or more and 8.0 mass % or less, further more preferably 0.10 mass % or more and 6.0 mass % or less, further more preferably 0.10 mass % or more and 2.5 mass % or less, and even more preferably 0.10 mass % or more and 2.0 mass % or less.

<39> The composition for forming a coating film according to any one of <1> to <38>, wherein a viscosity of the composition for forming a coating film at 25° C. is preferably 2 mPa·s or more, more preferably 5 mPa·s or more, further more preferably 10 mPa·s or more, further more preferably 30 mPa·s or more, further more preferably 50 mPa·s or more, and even more preferably 80 mPa·s or more, and preferably 3,000 mPa·s or less, more preferably 2,000 mPa·s or less, further more preferably 1,500 mPa·s or less, further more preferably 1,000 mPa·s or less, further more preferably 800 mPa·s or less, and even more preferably 500 mPa·s or less, and preferably 2 mPa·s or more and 3,000 mPa·s or less, more preferably 5 mPa·s or more and 2,000 mPa·s or less, more preferably 10 mPa·s or more and 1,500 mPa·s or less, further more preferably 30 mPa·s or more and 1,000 mPa·s or less, further more preferably 50 mPa·s or more and 800 mPa·s or less, and even more preferably 80 mPa·s or more and 500 mPa·s or less.

<40> The composition for forming a coating film according to any one of <1> to <39>, used in combination with a skincare cosmetic applied to the skin by a device other than an electrostatic spray.

<41> The composition for forming a coating film according to <40>, wherein the skincare cosmetic is selected from the group consisting of a skin lotion, a milky lotion, a cream, and a serum.

EXAMPLES

Hereinafter, the present invention is described in more detail in reference to Examples. However, the scope of the present invention is not limited to these Examples. "%" means "mass %" unless otherwise specified.

Test Example 1

Examples 1-1 to 1-10, Comparative Examples 1-1 to 1-6

(1) Preparation of the Composition for Forming a Coating Film

Polyvinyl butyral (manufactured by Sekisui Chemical Co., Ltd.: tradename; S-LEC B BM-1) was used as Component (a) and 99.5% ethanol (manufactured by Wako Pure Chemical Corporation) was used as Component (b) for the composition for forming a coating film. The component shown in Table 1 was used as Component (c) and the components shown in Table 1 were used as Component (d). Distearyldimonium chloride (manufactured by Evonik Japan Co., Ltd.: tradename; Varisoft TA100) was used as a conductivity controlling agent. The content of each component shown in Table 1 is an effective amount and the unit is mass %.

Component (b), Component (c), and Component (d) were each weighed and added to a 500 mL-SUS304 measuring cup (manufactured by Trusco Nakayama Corporation) and mixed by stirring for five minutes at room temperature (20° C. to 30° C.) using a propeller mixer (manufactured by Shinto Scientific Co., Ltd.: Fine Three-One Motor FBL600). For this operation, an SUS304 three-blade propeller was used (impeller blade diameter 60 mm, each blade is not perpendicular to, but angled against, an agitator shaft), and a rotation speed of propeller mixer was 100 rpm. After mixing by stirring for five minutes, the conductivity controlling agent separately weighed was added while stirring the mixed solution, and mixing by stirring for 5 more minutes to thoroughly dissolve the conductivity controlling agent thereby obtaining a clear homogeneous solution. Component (a) separately weighed was gradually added over a period of five minutes while stirring the obtained mixed solution, and a rotation speed of the propeller mixer was changed to 300 rpm at the time of finishing the addition of all of Component (a), followed by mixing by stirring for ten more hours thereby obtaining a homogeneous clear solution. This was considered as the composition for forming a coating film. The preparative scale of the composition for forming a coating film was 300 g in terms of the total weight of the composition for forming a coating film. The examples in which the conductivity controlling agent was not used did not carry out the dissolution step of the conductivity controlling agent.

(2) Viscosity of the Composition for Forming a Coating Film

The composition for forming a coating film was, after produced, stored in a water bath for 24 hours at 25° C. and measured for a viscosity at a measurement temperature of 25° C. using a B-type viscometer. The measurement temperature herein refers to a temperature of the composition for forming a coating film. The measurement was carried out using a B-type viscometer (TVB-10M) manufactured by Toki Sangyo Co., Ltd. as the B-type viscometer, with the rotor type of M2 at a rotation speed of 60 rpm. The measurement results are shown in Table 1.

(3) Skincare Cosmetic Application Step

A skin lotion and a milky lotion, or a skin lotion and a cream, were each applied to the inner side of the human forearm (4×5 cm) or the human face cheeks (5×7 cm) by the index finger before the electrostatic spray step. The skin lotion, milky lotion, and cream used are as follows. The skin lotion, milky lotion, and cream were used by weighing an amount used using a 1 mL of Terumo Syringe (SS-01T).

Applied sites: inner side of the human forearm (4×5 cm), two sites/one arm
: human face cheeks (5×7 cm), two sites/total of left and right
Skin lotion: Sofina beaute high moisturizing skin lotion (very rich)
(manufactured by Kao Corporation); 0.0015 mL/cm$^2$
Milky lotion: Alblanc Medicated Emulsion IV
(manufactured by Kao Corporation); 0.001 mL/cm$^2$
Cream: est Eternal Flow Cream
(manufactured by Kao Corporation); 0.001 mL/cm$^2$ (4) Electrostatic Spray Step The above composition for forming a coating film was applied by an electrostatic spray to the sites to which the above skincare cosmetics were applied using the electrostatic spray apparatus 10 having the structure shown in FIG. 1 and the appearance shown in FIG. 2. That is, the above composition for forming a coating film was applied by an electrostatic spray to the skin to which the above skincare cosmetics were applied thereby forming a coating film composed of fibers. The conditions under which the composition for forming a coating film was applied by the electrostatic spray were as follows.

Applied sites: inner side of the human forearm (4×5 cm), two sites/one arm (the sites to which the above skincare cosmetics were applied)
: human face cheeks (5×7 cm), two sites/total of left and right (the sites to which the above skincare cosmetics were applied)
Electrostatic spray application time: 20 seconds (inner side of the human forearm), 35 seconds (human face cheeks)
Discharge speed of the composition for forming a coating film: 0.1 g/min
Distance between the skin and the nozzle tip from which the composition for forming a coating film is discharged: 80 mm
Application environment: 20° C., 40% RH
Applied voltage: 10 kV (5) Evaluation (Compatibility of the Skincare Cosmetics With the Coating Film Composed of Fibers Formed by the Electrostatic Spray)

The coating films composed of fibers formed by the electrostatic spray on the skin after the skincare cosmetics were applied in Examples 1-1 to 1-10 and Comparative Examples 1-1 to 1-6 were evaluated for the compatibility of the skincare cosmetics with the coating film. The evaluation was carried out by applying the composition for forming a coating film by the electrostatic spray to the skin immediately after application of the skincare cosmetics thereby forming a coating film composed of fibers, and a state in which the skincare cosmetics and the coating film have come to thoroughly compatible since the time at which the formation of the coating film had been finished was visually observed. The evaluation sites were the inner side of the human forearm. The thorough compatibility of the skincare cosmetics with the coating film herein refers to a state in which the coating film was visually colorless and clear. In the present evaluation, the coating film was never touched by hands or fingers unless otherwise specified. The evaluation results are shown Table 1. The evaluation criteria are as follows.

6: Compatibility first appeared during the formation of the coating film by the electrostatic spray, and the skincare cosmetics and the coating film were thoroughly compatible at the time of finishing the formation of the coating film by the electrostatic spray.
5: Time for the skincare cosmetics and the coating film to have come to thoroughly compatible is shorter than Comparative Example 1.
4: Time for the skincare cosmetics and the coating film to have come to thoroughly compatible is substantially equivalent to Comparative Example 1.
3: Time for the skincare cosmetics and the coating film to have come to thoroughly compatible is longer than Comparative Example 1.
2: The skincare cosmetics and the coating film are not thoroughly compatible but the thorough compatibility can be achieved when the coating film was lightly pressed down by hand from thereon.
1: The skincare cosmetics and the coating film are not thoroughly compatible, and the thorough compatibility cannot be achieved even when the coating film was lightly pressed down by hand from thereon.

(Scratch Resistance)

The coating films composed of fibers formed by the electrostatic spray on the skin after the skincare cosmetics were applied in Examples 1-1 to 1-10 and Comparative Examples 1-1 to 1-6 were evaluated for the coating film scratch resistance. The evaluation was carried out by applying the composition for forming a coating film by the electrostatic spray to the skin immediately after application of the skincare cosmetics thereby forming a coating film composed of fibers, lightly pressing down the coating film by hand from thereon to achieve thorough compatibility, and subsequently touching by the index finger from a direction perpendicular to the skin to which the coating film was applied and reciprocating the index finger in a direction parallel to the skin to which the coating film was applied, thereby applying a shear force to the coating film, followed by visually observing a state of the coating film thereafter. The evaluation sites were the inner side of the human forearm. The thorough compatibility of the skincare cosmetics with the coating film herein refers to a state in which the coating film was visually colorless and clear. The evaluation results are shown Table 1. The evaluation criteria are as follows.

5: The coating film did not break and the coating film or the fibers forming the coating film were not peeled off even when a shear force was applied in a direction parallel to the skin to which the coating film was applied.
4: The coating film did not break but the coating film or the fibers forming the coating film were partially peeled off when a shear force was applied in a direction parallel to the skin to which the coating film was applied.

3: The coating film did not break but the entire coating film was substantially peeled off when a shear force was applied in a direction parallel to the skin to which the coating film was applied.
2: The coating film partially broke and the coating film or the fibers forming the coating film were partially peeled off when a shear force was applied in a direction parallel to the skin to which the coating film was applied.
1: The coating film broke and the entire coating film was substantially peeled off when a shear force was applied in a direction parallel to the skin to which the coating film was applied.

(Peelability of the Coating Film Composed of Fibers)

The coating films composed of fibers formed by the electrostatic spray on the skin after the skincare cosmetics were applied in Examples 1-1 to 1-10 and Comparative Examples 1-1 to 1-6 were evaluated for the coating film peelability. The evaluation was carried out by applying the composition for forming a coating film by the electrostatic spray to the skin immediately after application of the skincare cosmetics thereby forming a coating film composed of fibers, lightly pressing down the coating film by hand from thereon to achieve thorough compatibility, subsequently lightly scratching an end section of the coating film by the index finger to peel off about 2 to 3 mm, and peeling off the entire coating film while pulling up the peeled section in a direction perpendicular to the skin to which the coating film was applied, thereby visually observing the peeled state. The evaluation sites were the inner side of the human forearm. The thorough compatibility of the skincare cosmetics with the coating film herein refers to a state in which the coating film was visually colorless and clear. The evaluation results are shown Table 1. The evaluation criteria are as follows.

5: The coating film, as a single coating film, can be substantially completely removed in 1 peel.
4: After the start of peeling, the coating film had a cut in a direction parallel to the peeling direction but can be substantially completely removed in 2 to 3 peels as a single coating film.
3: After the start of peeling, the coating film had a cut in a direction parallel to the peeling direction or in a direction perpendicular to the peeling direction but can be substantially completely removed in 4 or more peels as a single coating film.
2: The coating film can be partially removed as a single coating film, but the fibers forming the coating film partially remained on the skin after the coating film was peeled off.
1: The coating film cannot be peeled off as a single coating film and cannot be removed unless scratched by fingers or washed with water.

(Filmy Feeling/Tight Feeling/Uncomfortable Feeling)

The coating films composed of fibers formed by the electrostatic spray on the skin after the skincare cosmetics were applied in Examples 1-1 to 1-10 and Comparative Examples 1-1 to 1-6 were evaluated for the filmy feeling/tight feeling/uncomfortable feeling. The evaluation was carried out by applying the composition for forming a coating film by the electrostatic spray to the skin immediately after application of the skincare cosmetics thereby forming a coating film composed of fibers, lightly pressing down the coating film by hand from thereon to achieve thorough compatibility, subsequently evaluating the filmy feeling/tight feeling/uncomfortable feeling by the sensory evaluation after the elapse of 10 min. The evaluation sites were the human face cheeks. The thorough compatibility of the skincare cosmetics with the coating film herein refers to a state in which the coating film was visually colorless and clear. The evaluation results are shown Table 1. The evaluation criteria are as follows.

5: No particular filmy feeling/tight feeling/uncomfortable feeling was sensed even when the coating film was attached on the skin at normal times, and the filmy feeling/tight feeling/uncomfortable feeling were not sensed when facial expressions changed thereby leading to a sensation with no difference from a coating-film free state.
4: No particular filmy feeling/tight feeling/uncomfortable feeling was sensed even when the coating film was attached on the skin at normal times, but the filmy feeling/tight feeling/uncomfortable feeling were slightly sensed when facial expressions changed however time can be spent without particular discomfort.
3: No particular filmy feeling/tight feeling/uncomfortable feeling was sensed even when the coating film was attached on the skin at normal times, but intense filmy feeling/tight feeling/uncomfortable feeling was sensed when facial expression changed thereby causing a discomfort.
2: Slight filmy feeling/tight feeling/uncomfortable feeling was sensed due to the coating film attached on the skin at normal times and intense filmy feeling/tight feeling/uncomfortable feeling was sensed particularly when facial expressions changed thereby causing a discomfort.
1: Intense filmy feeling/tight feeling/uncomfortable feeling was sensed due to the coating film attached on the skin at normal times causing a discomfort.

Evaluation results are shown in Table 1. The results of Table 1 reveal that the coating films formed using the composition for forming a coating film used in each Example are more likely to be compatible with the skincare cosmetics, have better scratch resistance, are easier to peel, and have a better impression from use such as filmy feeling, tight feeling, and uncomfortable feeling when compared with the coating films formed using the compositions for forming a coating film used in Comparative Examples.

TABLE 1

| Component | Component name | Example |  |  |  |  |  |  |  |  |  |
|---|---|---|---|---|---|---|---|---|---|---|---|
|  |  | 1-1 | 1-2 | 1-3 | 1-4 | 1-5 | 1-6 | 1-7 | 1-8 | 1-9 | 1-10 |
| (a) | Polyvinyl butyral (*1) | 12.0 | 12.0 | 11.9 | 11.9 | 11.7 | 12.2 | 11.7 | 12.2 | 12.5 | 12.1 |
| (b) | Ethanol (*2) | 80.0 | 80.0 | 79.6 | 79.6 | 77.8 | 81.3 | 77.8 | 81.3 | 83.0 | 80.9 |
| (c) | PEG-8 (*3) | 4.0 | 4.0 | 4.0 | 4.0 | 6.0 | 2.0 | 6.0 | 4.0 | 2.0 | 5.0 |
| (d) | Dimethicone (*4) | 4.0 | 4.0 | 4.0 | 4.0 | 4.0 | 4.0 | 2.0 | 2.0 | 2.0 | — |
|  | Di(phytosteryl/octyldodecyl) lauroyl glutamate (*5) | — | — | — | — | — | — | — | — | — | 2.0 |
| Conductivity controlling agent | Distearyldimonium chloride (*6) | — | — | 0.5 | 0.5 | 0.5 | 0.5 | 0.5 | 0.5 | 0.5 | 0.5 |
| Total |  | 100.0 | 100.0 | 100.0 | 100.0 | 100.0 | 100.0 | 98.0 | 100.0 | 100.0 | 100.5 |

TABLE 1-continued

|  |  |  |  |  |  |  |  |  |  |  |
|---|---|---|---|---|---|---|---|---|---|---|
| (a)/(c) | 3.0 | 3.0 | 3.0 | 3.0 | 2.0 | 6.1 | 2.0 | 3.1 | 6.3 | 2.4 |
| (c)/(d) | 1.0 | 1.0 | 1.0 | 1.0 | 1.5 | 0.5 | 3.0 | 2.0 | 1.0 | 2.5 |
| (a)/(d) | 3.0 | 3.0 | 3.0 | 3.0 | 2.9 | 3.1 | 5.9 | 6.1 | 6.3 | 6.1 |
| (a)/(b) | 0.15 | 0.15 | 0.15 | 0.15 | 0.15 | 0.15 | 0.15 | 0.15 | 0.15 | 0.15 |
| Viscosity of composition for forming a coating film (25° C.) (Unit: mPa · s) | 171.3 | 171.3 | 178.1 | 178.1 | 184.2 | 187.2 | 198.7 | 196.1 | 198.3 | 177.1 |
| Skincare cosmetic — Skin lotion (*7) | Applied | Applied | Applied | Applied | Applied | Applied | Applied | Applied | Applied | Applied |
| Milky lotion (*8) | Applied | — | Applied | — | Applied | Applied | Applied | Applied | Applied | Applied |
| Cream (*9) | — | Applied | — | Applied | — | — | — | — | — | — |
| Evaluation score — Compatibility of skincare cosmetic with coating film composed of fibers formed by electrostatic spray | 5 | 5 | 5 | 5 | 6 | 5 | 6 | 5 | 5 | 5 |
| Scratch resistance | 5 | 5 | 5 | 5 | 5 | 4 | 5 | 5 | 4 | 5 |
| Peelability of coating film composed of fibers | 4 | 4 | 4 | 4 | 5 | 4 | 5 | 4 | 4 | 5 |
| Filmy feeling/tight feeling/ uncomfortable feeling | 4 | 4 | 4 | 4 | 5 | 3 | 5 | 4 | 3 | 5 |

| Component | Component name | Comparative Example 1-1 | 1-2 | 1-3 | 1-4 | 1-5 | 1-6 |
|---|---|---|---|---|---|---|---|
| (a) | Polyvinyl butyral (*1) | 12.0 | 12.3 | 12.0 | 11.9 | 12.8 | 12.8 |
| (b) | Ethanol (*2) | 88.0 | 87.2 | 83.0 | 79.6 | 85.6 | 85.6 |
| (c) | PEG-8 (*3) | — | — | — | — | 1.1 | 1.1 |
| (d) | Dimethicone (*4) | — | — | — | 8.0 | — | — |
|  | Di(phytosteryl/octyldodecyl) lauroyl glutamate (*5) | — | — | 5.0 | — | — | — |
| Conductivity controlling agent | Distearyldimonium chloride (*6) | — | 0.5 | — | 0.5 | 0.5 | 0.5 |
| Total |  | 100.0 | 100.0 | 100.0 | 100.0 | 100.0 | 100.0 |
| (a)/(c) |  | — | — | — | — | 11.6 | 11.6 |
| (c)/(d) |  | — | — | — | — | — | — |
| (a)/(d) |  | — | — | 2.4 | 1.5 | — | — |
| (a)/(b) |  | 0.14 | 0.14 | 0.14 | 0.15 | 0.15 | 0.15 |
| Viscosity of composition for forming a coating film (25° C.) (Unit: mPa · s) |  | 145.4 | 143.6 | 161.8 | 165.7 | 197.3 | 197.3 |
| Skincare cosmetic — Skin lotion (*7) |  | Applied | Applied | Applied | Applied | Applied | Applied |
| Milky lotion (*8) |  | Applied | Applied | Applied | Applied | Applied | — |
| Cream (*9) |  | — | — | — | — | — | Applied |
| Evaluation score — Compatibility of skincare cosmetic with coating film composed of fibers formed by electrostatic spray |  | 4 | 4 | 3 | 4 | 3 | 3 |
| Scratch resistance |  | 2 | 2 | 2 | 2 | 2 | 2 |
| Peelability of coating film composed of fibers |  | 2 | 2 | 2 | 2 | 2 | 2 |
| Filmy feeling/tight feeling/ uncomfortable feeling |  | 2 | 2 | 2 | 2 | 2 | 2 |

(*1) S-LEC B BM-1 (manufactured by Sekisui Chemical Co., Ltd.)
(*2) 99.5% Ethanol (manufactured by Wako Pure Chemical Corporation)
(*3) PEG-400 (manufactured by Sanyo Chemical Industries, Ltd.)
(*4) KF-96A-6CS (manufactured by Shin-Etsu Chemical Co., Ltd.)
(*5) Eldew PS-203 (manufactured by Ajinomoto Co., Inc.)
(*6) Varisoft TA100 (manufactured by Evonik Japan Co., Ltd.)
(*7) Sofina beaute high moisturizing skin lotion (very rich) (manufactured by Kao Corporation)
(*8) Alblanc Medicated Emulsion IV (manufactured by Kao Corporation)
(*9) est Eternal Flow Cream (manufactured by Kao Corporation)

Test Example 2

Examples 2-1 to 2-8, Comparative Examples 2-1 to 2-5

(1) Preparation of the composition for forming a coating film

The compositions for forming a coating film were prepared by the same method as [Test Example 1].

(2) Viscosity of the composition for forming a coating film

The viscosity of the compositions for forming a coating film was measured by the same method as [Test Example 1].

(3) Skincare cosmetic application step

The skincare cosmetic was not used in [Test Example 2].

(4) Electrostatic spray step

This step was carried out by the same method as [Test Example 1] except that the skincare formulation was not used in the method described in [Test Example 1].

(5) Evaluation (Scratch Resistance)

The evaluation was carried out by the same method as [Test Example 1] except that the skincare formulation was not used in the method described in [Test Example 1]. The evaluation results are shown in Table 2.

(Peelability of the Coating Film Composed of Fibers)

The evaluation was carried out by the same method as [Test Example 1] except that the skincare formulation was not used in the method described in [Test Example 1]. The evaluation results are shown in Table 2.

(Filmy Feeling, Tight Feeling and Uncomfortable Feeling)

The evaluation was carried out by the same method as [Test Example 1] except that the skincare formulation was not used in the method described in [Test Example 1]. The evaluation results are shown in Table 2.

TABLE 2

| | | Example | | | | | | | |
|---|---|---|---|---|---|---|---|---|---|
| Component | Component name | 2-1 | 2-2 | 2-3 | 2-4 | 2-5 | 2-6 | 2-7 | 2-8 |
| (a) | Polyvinyl butyral (*1) | 12.0 | 11.9 | 11.7 | 12.2 | 11.7 | 12.2 | 12.5 | 12.1 |
| (b) | Ethanol (*2) | 80.0 | 79.6 | 77.8 | 81.3 | 77.8 | 81.3 | 83.0 | 80.9 |
| (c) | PEG-8 (*3) | 4.0 | 4.0 | 6.0 | 2.0 | 6.0 | 4.0 | 2.0 | 5.0 |
| (d) | Dimethicone (*4) | 4.0 | 4.0 | 4.0 | 4.0 | 2.0 | 2.0 | 2.0 | — |
| | Di(phytosteryl/octyldodecyl) lauroyl glutamate (*5) | — | — | — | — | — | — | — | 2.0 |
| Conductivity controlling agent | Distearyldimonium chloride (*6) | — | 0.5 | 0.5 | 0.5 | 0.5 | 0.5 | 0.5 | 0.5 |
| Total | | 100.0 | 100.0 | 100.0 | 100.0 | 98.0 | 100.0 | 100.0 | 100.5 |
| (a)/(c) | | 3.0 | 3.0 | 2.0 | 6.1 | 2.0 | 3.1 | 6.3 | 2.4 |
| (c)/(d) | | 1.0 | 1.0 | 1.5 | 0.5 | 3.0 | 2.0 | 1.0 | 2.5 |
| (a)/(d) | | 3.0 | 3.0 | 2.9 | 3.1 | 5.9 | 6.1 | 6.3 | 6.1 |
| (a)/(b) | | 0.15 | 0.15 | 0.15 | 0.15 | 0.15 | 0.15 | 0.15 | 0.15 |
| Viscosity of composition for forming a coating film (25° C.) (Unit: mPa · s) | | 171.3 | 178.1 | 184.2 | 187.2 | 198.7 | 196.1 | 198.3 | 177.1 |
| Evaluation score | Scratch resistance | 5 | 5 | 5 | 4 | 5 | 5 | 4 | 5 |
| | Peelability of coating film composed of fibers | 5 | 5 | 5 | 4 | 5 | 5 | 4 | 5 |
| | Filmy feeling/tight feeling/ uncomfortable feeling | 3 | 3 | 4 | 3 | 4 | 3 | 3 | 4 |

| | | | Comparative Example | | | | |
|---|---|---|---|---|---|---|---|
| | Component | Component name | 2-1 | 2-2 | 2-3 | 2-4 | 2-5 |
| | (a) | Polyvinyl butyral (*1) | 12.0 | 12.3 | 12.0 | 11.9 | 12.8 |
| | (b) | Ethanol (*2) | 88.0 | 87.2 | 83.0 | 79.6 | 85.6 |
| | (c) | PEG-8 (*3) | — | — | — | — | 1.1 |
| | (d) | Dimethicone (*4) | — | — | — | 8.0 | — |
| | | Di(phytosteryl/octyldodecyl) lauroyl glutamate (*5) | — | — | 5.0 | — | — |
| | Conductivity controlling agent | Distearyldimonium chloride (*6) | — | 0.5 | — | 0.5 | 0.5 |
| | Total | | 100.0 | 100.0 | 100.0 | 100.0 | 100.0 |
| | (a)/(c) | | — | — | — | — | 11.6 |
| | (c)/(d) | | — | — | — | — | — |
| | (a)/(d) | | — | — | 2.4 | 1.5 | — |
| | (a)/(b) | | 0.14 | 0.14 | 0.14 | 0.15 | 0.15 |
| | Viscosity of composition for forming a coating film (25° C.) (Unit: mPa · s) | | 145.4 | 143.6 | 161.8 | 165.7 | 197.3 |
| | Evaluation score | Scratch resistance | 1 | 1 | 1 | 1 | 1 |
| | | Peelability of coating film composed of fibers | 1 | 1 | 1 | 1 | 1 |
| | | Filmy feeling/tight feeling/ uncomfortable feeling | 1 | 1 | 1 | 1 | 1 |

(*1) S-LEC B BM-1 (manufactured by Sekisui Chemical Co., Ltd.)
(*2) 99.5% Ethanol (manufactured by Wako Pure Chemical Corporation)
(*3) PEG-400 (manufactured by Sanyo Chemical Industries, Ltd.)
(*4) KF-96A-6CS (manufactured by Shin-Etsu Chemical Co., Ltd.)
(*5) Eldew PS-203 (manufactured by Ajinomoto Co., Inc.)
(*6) Varisoft TA100 (manufactured by Evonik Japan Co., Ltd.)

The evaluation results are shown in Table 2. The results of Table 2 reveal that the coating films formed using the composition for forming a coating film used in each Example have better scratch resistance and are easier to peel when compared with the coating films formed using the compositions for forming a coating film used in Comparative Examples.

Test Example 3

Examples 3-1 to 3-2, Comparative Examples 3-1

(1) Preparation of the Composition for Forming a Coating Film

The compositions for forming a coating film were prepared by the same method as [Test Example 1].

(2) Viscosity of the Composition for Forming a Coating Film

Viscosity of the compositions for forming a coating film was measured by the same method as [Test Example 1].

(3) Skincare Cosmetic Application Step

The skincare cosmetics were applied by the same method as [Test Example 1]. The evaluation sites were the inner side of the human forearm, and the skincare cosmetics used were the skin lotion and the milky lotion described in [Test Example 1].

4) Electrostatic Spray Step

This step was carried out by the same method as [Test Example 1].

(5) Evaluation

The coating films composed of fibers formed by the electrostatic spray on the skin after the skincare cosmetics were applied in Examples were evaluated for impression from use. Evaluation included five items composed of stickiness, oily feeling, friction feeling, and smoothness. The evaluation sites were the inner side of the human forearm. The evaluation was carried out by the sensory evaluation by five expert panelists and the average values of the five panelists were used as the evaluation scores. The evaluation score of the skin to which only the skincare cosmetics were applied was "0" and the evaluation scores were comparative evaluation thereto. The scores included seven scales consisting of −3, −2, −1, 0, 1, 2, and 3. The evaluation on the stickiness was made for slight stickiness as +evaluation, whereas for intense stickiness as −evaluation, the evaluation on the oily feeling was made for slightly oily feeling as +evaluation, whereas for intense oily feeling as −evaluation, the evaluation on the friction feeling was made for slight friction feeling as +evaluation, whereas for intense friction feeling as −evaluation, and the evaluation on the smoothness was made for intense smoothness as +evaluation whereas for slight smoothness as −evaluation. The evaluation results are shown in Table 3.

TABLE 3

| Component | Component name | Example 3-1 | Example 3-2 | Comparative Example 3-1 |
|---|---|---|---|---|
| (a) | Polyvinyl butyral (*1) | 12.0 | 12.1 | — |
| (b) | Ethanol (*2) | 80.0 | 80.9 | — |
| (c) | PEG-8 (*3) | 4.0 | 5.0 | — |
| (d) | Dimethicone (*4) | 4.0 | — | — |
|  | Di(phytosteryl/octyldodecyl) lauroyl glutamate (*5) | — | 2.0 | — |
| Conductivity controlling agent | Distearyldimoniunn chloride (*6) | — | — | — |
|  | Total | 100.0 | 100.0 | — |
|  | (a)/(c) | 3.0 | 2.4 | — |
|  | (c)/(d) | 1.0 | 2.5 | — |
|  | (a)/(d) | 3.0 | 6.1 | — |
|  | (a)/(b) | 0.15 | 0.15 | — |
| Viscosity of composition for forming a coating film (25° C.) (Unit: mPa · s) |  | 178.1 | 177.1 | — |
| Evaluation score | Stickiness | 2.0 | 0.2 | 0.0 |
|  | Oily feeling | 2.0 | 1.6 | 0.0 |
|  | Friction feeling | 0.8 | 0.2 | 0.0 |
|  | Smoothness | 1.4 | 1.4 | 0.0 |

*1) S-LEC B BM-1 (manufactured by Sekisui Chemical Co., Ltd.)
*2) 99.5% Ethanol (manufactured by Wako Pure Chemical Corporation)
*3) PEG-400 (manufactured by Sanyo Chemical Industries, Ltd.)
*4) KF-96A-6C5 (manufactured by Shin-Etsu Chemical Co., Ltd.)
*5) Eldew PS-203 (manufactured by Ajinomoto Co., Inc.)
*6) Varisoft TA100 (manufactured by Evonik Japan Co., Ltd.)

The evaluation results are shown in Table 3. The results of Table 3 reveal that an impression from use can be instantly changed by the coating films formed using the composition for forming a coating film used in each Example when combined with the skincare cosmetics.

Test Example 4

Examples 4-1 to 4-18, Comparative Examples 4-1 to 4-2

(1) Preparation of the Composition for Forming a Coating Film

The compositions for forming a coating film were prepared by the same method as [Test Example 1]. Polyvinyl butyral (manufactured by Sekisui Chemical Co., Ltd.: tradename; S-LEC B BM-1) was used as Component (a) and 99.5% ethanol (manufactured by Wako Pure Chemical Corporation) was used as Component (b) of the composition for forming a coating film. The components shown in Table 4 and Table 5 were used as Component (c) and Component (d). The contents of each component shown in Table 4 and Table 5 are effective amounts and the unit is mass %.

(2) Viscosity of the Composition for Forming a Coating Film

The viscosity of the compositions for forming a coating film was measured by the same method as [Test Example 1].

(3) Electrostatic Spray Step

The above composition for forming a coating film was applied by the electrostatic spray to an application subject using the electrostatic spray apparatus 10 having the structure shown in FIG. 1 and the appearance shown in FIG. 2. The conditions under which the electrostatic spray was applied were as follows.

Applied voltage: 10 kV

Discharge speed of the composition for forming a coating film: 0.1 g/min

Distance between the application subject and the nozzle tip from which the composition for forming a coating film is discharged: 80 mm Application period of time: 30 seconds Application environment: 30° C., 80° RH Application subject: aluminum foil (tradename: My Foil, manufactured by UACJ foil)

(4) Evaluation

The spraying performance (spinning performance) of the electrostatic spray was evaluated by the following criteria.

A: Stable spinning with favorable film formability.

B: Slightly unstable spinning slightly with flocculation during film formation.

C: Unstable spinning with droplets spattering during spinning, or the composition for forming a coating film not always landing on the application subject.

TABLE 4

| Component | Component name | Example 4-1 | 4-2 | 4-3 | 4-4 | 4-5 | 4-6 | 4-7 | 4-8 | 4-9 | 4-10 | 4-11 |
|---|---|---|---|---|---|---|---|---|---|---|---|---|
| (a) | Polyvinyl butyral (*1) | 12.0 | 12.0 | 12.0 | 12.0 | 12.0 | 12.0 | 12.0 | 12.0 | 12.0 | 12.0 | 12.0 |
| (b) | Ethanol (*2) | 55.0 | 70.0 | 60.0 | 75.0 | 70.0 | 65.0 | 64.0 | 64.0 | 70.0 | 73.0 | 70.0 |
| (c) | PEG-8 (*3) | 4.0 | 4.0 | 4.0 | 4.0 | 4.0 | 4.0 | 4.0 | 4.0 | 4.0 | 5.0 | 4.0 |
| (d) | Dimethicone (*4) | 4.0 | 4.0 | 4.0 | 4.0 | 4.0 | 4.0 | 10.0 | | | | |
| | Dimethicone (*5) | | | | | | | | 10.0 | 7.0 | 5.0 | 4.0 |
| | Isododecane (*6) | 25.0 | 10.0 | | | | | | | | | |
| | Neopentyl glycol dicaprate (*7) | | | 20.0 | 5.0 | 10.0 | 15.0 | 10.0 | 10.0 | 7.0 | 5.0 | 10.0 |
| | Neopentyl glycol diethylhexanoate (*8) | | | | | | | | | | | |
| | Isononyl isononanoate (*9) | | | | | | | | | | | |
| | Isotridecyl isononanoate (*10) | | | | | | | | | | | |
| Conductivity controlling agent | Distearyldimonium chloride (*11) | | | | | | | | | | | |
| Total | | 100.0 | 100.0 | 100.0 | 100.0 | 100.0 | 100.0 | 100.0 | 100.0 | 100.0 | 100.0 | 100.0 |
| (a)/(c) | | 3.0 | 3.0 | 3.0 | 3.0 | 3.0 | 3.0 | 3.0 | 3.0 | 3.0 | 2.4 | 3.0 |
| (c)/(d) | | 0.14 | 0.29 | 0.17 | 0.44 | 0.29 | 0.21 | 0.20 | 0.20 | 0.29 | 0.50 | 0.29 |
| (a)/(d) | | 0.41 | 0.86 | 0.50 | 1.33 | 0.86 | 0.63 | 0.60 | 0.60 | 0.86 | 1.20 | 0.86 |
| (a)/(b) | | 0.22 | 0.17 | 0.20 | 0.16 | 0.17 | 0.18 | 0.19 | 0.19 | 0.17 | 0.16 | 0.17 |
| Viscosity of composition for forming a coating film (25° C.) (Unit: mPa · s) | | 203.9 | 192.3 | 273.8 | 174.5 | 202.8 | 235.8 | 237.6 | 233.9 | 184.8 | 187.2 | 205.9 |
| Evaluation score | Spinning performance | A | A | A | B | A | A | A | A | A | B | A |

TABLE 5

| Component | Component name | Example 4-12 | 4-13 | 4-14 | 4-15 | 4-16 | 4-17 | 4-18 | Comparative Example 4-1 | 4-2 |
|---|---|---|---|---|---|---|---|---|---|---|
| (a) | Polyvinyl butyral (*1) | 12.0 | 12.0 | 12.0 | 12.0 | 12.0 | 12.0 | 12.0 | 12.0 | 12.0 |
| (b) | Ethanol (*2) | 71.0 | 70.0 | 69.0 | 70.0 | 70.0 | 70.0 | 70.0 | 88.0 | 87.5 |
| (c) | PEG-8 (*3) | 5.0 | 5.0 | 5.0 | 4.0 | 4.0 | 4.0 | 4.0 | | |
| (d) | Dimethicone (*4) | | | | | | | | | |
| | Dimethicone (*5) | 6.0 | 7.0 | 7.0 | 7.0 | 7.0 | 7.0 | | | |
| | Isododecane (*6) | | | | | | | | | |
| | Neopentyl glycol dicaprate (*7) | 6.0 | 6.0 | 7.0 | | | | 14.0 | | |
| | Neopentyl glycol diethylhexanoate (*8) | | | | 7.0 | | | | | |
| | Isononyl isononanoate (*9) | | | | | 7.0 | | | | |
| | Isotridecyl isononanoate (*10) | | | | | | 7.0 | | | |
| Conductivity controlling agent | Distearyldimonium chloride (*11) | | | | | | | | | 0.5 |
| Total | | 100.0 | 100.0 | 100.0 | 100.0 | 100.0 | 100.0 | 100.0 | 100.0 | 100.0 |
| (a)/(c) | | 2.4 | 2.4 | 2.4 | 3.0 | 3.0 | 3.0 | 3.0 | — | — |
| (c)/(d) | | 0.42 | 0.38 | 0.36 | 0.29 | 0.29 | 0.29 | 0.29 | — | — |
| (a)/(d) | | 1.00 | 0.92 | 0.86 | 0.86 | 0.86 | 0.86 | 0.86 | — | — |
| (a)/(b) | | 0.17 | 0.17 | 0.17 | 0.17 | 0.17 | 0.17 | 0.17 | 0.14 | 0.14 |
| Viscosity of composition for forming a coating film (25° C.) (Unit: mPa · s) | | 183.2 | 194.3 | 198.9 | 202.3 | 199.3 | 205.9 | 211.3 | 145.4 | 143.6 |
| Evaluation score | Spinning performance | B | B | A | A | A | A | A | C | C |

(*1) S-LEC B BM-1 (manufactured by Sekisui Chemical Co., Ltd.)
(*2) 99.5% Ethanol (manufactured by Wako Pure Chemical Corporation)
(*3) PEG-400 (manufactured by Sanyo Chemical Industries, Ltd.)
(*4) KF-96A-6CS (manufactured by Shin-Etsu Chemical Co., Ltd.)
(*5) KF-96L-2CS (manufactured by Shin-Etsu Chemical Co., Ltd.)
(*6) Marukazole R (manufactured by Maruzen Petrochemical Co., Ltd.)
(*7) Estemol N-01 (manufactured by The Nisshin OilliO Group, Ltd.)
(*8) Cosmol 525 (manufactured by The Nisshin OilliO Group, Ltd.)
(*9) Salacos 99 (manufactured by The Nisshin OilliO Group, Ltd.)
(*10) Salacos 913 (manufactured by The Nisshin OilliO Group, Ltd.)
(*11) Varisoft TA100 (manufactured by Evonik Japan Co., Ltd.)

The evaluation results are shown in Table 4 and Table 5. The results of Table 4 and Table 5 reveal that the coating films formed using the composition for forming a coating film used in each Example had good spinning stability.

Test Example 5

Examples 5-1 to 5-8, Comparative Examples 5-1 to 5-2

(1) Preparation of the Composition for Forming a Coating Film

The compositions for forming a coating film were prepared by the same method as [Test Example 4].

(2) Electrostatic Spray Step

The composition for forming a coating film was applied by the electrostatic spray to an application subject using the electrostatic spray apparatus 10 having the structure shown in FIG. 1 and the appearance shown in FIG. 2. The conditions under which the electrostatic spray was applied were as follows. The electrostatic spray was applied homogeneously throughout the entire application subject.

Applied voltage: 10 kV
Discharge speed of the composition for forming a coating film: 0.1 g/min
Distance between the application subject and the nozzle tip from which the composition for forming a coating film is discharged: 80 mm
Application period of time: 40 seconds
Application environment: 25° C., 30% RH
Application subject: artificial leather (12×7 cm, manufactured by Okamoto Industries, Inc.)

(3) Evaluation (Scratch Resistance)

The coating film composed of fibers was formed on the application subject in the above electrostatic spray step and evaluated for the scratch resistance. The evaluation was carried out by placing cotton fibers (13×8 cm) on the application subject on which the coating film composed of fibers was formed in the above electrostatic spray step, and further placing a 100 g weight on top thereof, followed by moving the weight together with the cotton fibers in a horizontal direction of the long side of the application subject while applying a load to the application subject thereby evaluating the scratch resistance. The evaluation was carried out in such a way as to move the weight 12 cm in a direction of the long side of the application subject. In the case where the coating film composed of fibers did not break when scratched with a load of 100 g, the same scratch resistance evaluation was carried out with a weight of 200 g. The weight was changed to 300 g, 400 g, and 500 g in the same procedure and the load at which the coating film composed of fibers broke was evaluated. The evaluation criteria are as follows.

6: The coating film composed of fibers did not break with a load of 500 g.
5: The coating film composed of fibers broke with a load of 500 g.
4: The coating film composed of fibers broke with a load of 400 g.
3: The coating film composed of fibers broke with a load of 300 g.
2: The coating film composed of fibers broke with a load of 200 g.
1: The coating film composed of fibers broke with a load of 100 g.

(Peelability of the Coating Film Composed of Fibers)

A coating film composed of fibers was formed on the application subject in the above electrostatic spray step and evaluated for the peelability of the coating film composed of fibers. The evaluation was carried out by peeling off an end section by about 2 to 3 mm of the coating film composed of fibers formed on the application subject in the above electrostatic spray step, peeling off the entire coating film while pulling up the peeled section in a direction perpendicular to the application subject to which the coating film was applied, thereby visually observing the peeled state. The section to be peeled first was peeled off entirely by about 2 to 3 mm at the end section of the short side section of the application subject. The evaluation criteria are as follows.

5: The coating film, as a single coating film, can be substantially completely removed in 1 peel.
4: After the start of peeling, the coating film had a cut in a direction parallel to the peeling direction but can be substantially completely removed in 2 to 3 peels as a single coating film.
3: After the start of peeling, the coating film had a cut in a direction parallel to the peeling direction or in a direction perpendicular to the peeling direction but can be substantially completely removed in 4 or more peels as a single coating film.
2: The coating film can be partially removed as a single coating film, but the fibers forming the coating film partially remained on the artificial leather after the coating film was peeled off.
1: The coating film cannot be peeled off as a single coating film and cannot be removed unless scratched by fingers or washed with water.

TABLE 6

| | | Example | | | | | | | | Comparative Example | |
|---|---|---|---|---|---|---|---|---|---|---|---|
| Component | Component name | 5-1 | 5-2 | 5-3 | 5-4 | 5-5 | 5-6 | 5-7 | 5-8 | 5-1 | 5-2 |
| (a) | Polyvinyl butyral (*1) | 12.0 | 12.0 | 12.0 | 12.0 | 12.0 | 12.0 | 12.0 | 12.0 | 12.0 | 12.0 |
| (b) | Ethanol(*2) | 55.0 | 75.0 | 65.0 | 70.0 | 70.0 | 70.0 | 70.0 | 70.0 | 88.0 | 87.5 |
| (c) | PEG-8 (*3) | 4.0 | 4.0 | 4.0 | 4.0 | 4.0 | 4.0 | 4.0 | 4.0 | | |
| (d) | Dimethicone (*4) | 4.0 | 4.0 | 4.0 | | | | | | | |
| | Dimethicone (*5) | | | | 7.0 | 7.0 | 7.0 | 7.0 | | | |
| | Isododecane (*6) | 25.0 | | | | | | | | | |
| | Neopentyl glycol dicaprate (*7) | | 5.0 | 15.0 | 7.0 | | | | | 14.0 | |
| | Neopentyl glycol diethylhexanoate (*8) | | | | | 7.0 | | | | | |
| | Isononyl isononanoate (*9) | | | | | | | 7.0 | | | |
| | Isotridecyl isononanoate (*10) | | | | | | | | 7.0 | | |

TABLE 6-continued

| Component | Component name | Example 5-1 | 5-2 | 5-3 | 5-4 | 5-5 | 5-6 | 5-7 | 5-8 | Comparative Example 5-1 | 5-2 |
|---|---|---|---|---|---|---|---|---|---|---|---|
| Conductivity controlling agent | Distearyldimonium chloride (*11) | | | | | | | | | | 0.5 |
| Total | | 100.0 | 100.0 | 100.0 | 100.0 | 100.0 | 100.0 | 100.0 | 100.0 | 100.0 | 100.0 |
| (a)/(c) | | 3.0 | 3.0 | 3.0 | 3.0 | 3.0 | 3.0 | 3.0 | 3.0 | — | — |
| (c)/(d) | | 0.14 | 0.44 | 0.21 | 0.29 | 0.29 | 0.29 | 0.29 | 0.29 | — | — |
| (a)/(d) | | 0.41 | 1.33 | 0.63 | 0.86 | 0.86 | 0.86 | 0.86 | 0.86 | — | — |
| (a)/(b) | | 0.22 | 0.16 | 0.18 | 0.17 | 0.17 | 0.17 | 0.17 | 0.17 | 0.14 | 0.14 |
| Evaluation score | Scratch resistance | 6 | 6 | 6 | 6 | 6 | 6 | 6 | 6 | 2 | 1 |
| | Peelability of coating film composed of fibers | 5 | 5 | 4 | 5 | 5 | 4 | 5 | 4 | 2 | 1 |

(*1) S-LEC B BM-1 (manufactured by Sekisui Chemical Co., Ltd.)
(*2) 99.5% Ethanol (manufactured by Wako Pure Chemical Corporation)
(*3) PEG-400 (manufactured by Sanyo Chemical Industries, Ltd.)
(*4) KF-96A-6CS (manufactured by Shin-Etsu Chemical Co., Ltd.)
(*5) KF-96L-2CS (manufactured by Shin-Etsu Chemical Co., Ltd.)
(*6) Marukazole R (manufactured by Maruzen Petrochemical Co., Ltd.)
(*7) Estemol N-01 (manufactured by The Nisshin OilliO Group, Ltd.)
(*8) Cosmol 525 (manufactured by The Nisshin OilliO Group, Ltd.)
(*9) Salacos 99 (manufactured by The Nisshin OilliO Group, Ltd.)
(*10) Salacos 913 (manufactured by The Nisshin OilliO Group, Ltd.)
(*11) Varisoft TA100 (manufactured by Evonik Japan Co., Ltd.)

The evaluation results are shown in Table 6. The results of Table 6 reveal that the coating films formed using the composition for forming a coating film used in each Example have good scratch resistance and peelability of the coating films composed of fibers.

Test Example 6

Examples 6-1, Comparative Example 6-1

(1) Preparation of the composition for forming a coating film

Polyurethane (manufactured by Covestro AG: tradename; Baycusan C2000) was used as Component (a) and 99.5% ethanol (manufactured by Wako Pure Chemical Corporation) was used as Component (b) of the composition for forming a coating film. The components shown in Table 7 were used as Component (c) and Component (d). The content of each component shown in Table 7 is an effective amount and the unit is mass %.

Component (a), Component (b), Component (c), and Component (d) were each weighed and added to a 200 mL-SUS304 measuring cup (manufactured by Trusco Nakayama Corporation) and mixed by stirring for five minutes at room temperature (20° C. to 30° C.) using a propeller mixer (manufactured by Shinto Scientific Co., Ltd.: Fine Three-One Motor FBL600). For this operation, an SUS304 three-blade propeller was used (impeller blade diameter 60 mm, each blade is not perpendicular to, but angled against, an agitator shaft), and a rotation speed of propeller mixer was 100 rpm, thereby obtaining a clear homogeneous solution. This was considered as the composition for forming a coating film. The preparative scale of the composition for forming a coating film was 100 g in terms of the total weight of the composition for forming a coating film. The polyurethane used as Component (a) was a commercially available 40 mass % ethanol solution.

(2) Viscosity of the Composition for Forming a Coating Film

The viscosity of the compositions for forming a coating film was measured by the same method as [Test Example 1].

(3) Electrostatic Spray Step and Evaluation Method for the Spray Performance of the Electrostatic Spray The electrostatic spray was applied by the same method as [Test Example 4] and the spray performance of the electrostatic spray was evaluated by the same method as [Test Example 4].

(4) Electrostatic Spray Step, and Evaluation Method for the Scratch Resistance and Peelability of the Coating Film Composed of Fibers The electrostatic spray was applied by the same method as [Test Example 5], and the scratch resistance and peelability of the coating film composed of fibers were evaluated by the same method as [Test Example 5].

TABLE 7

| Component | Component name | Example 6-1 | Comparative Example 6-1 |
|---|---|---|---|
| (a) | Polyurethane (*12) | 24.0 | 24.0 |
| (b) | Ethanol (*2) | 60.0 | 76.0 |
| (c) | PEG-8 (*3) | 8.0 | |
| (d) | Dimethicone (*4) | 8.0 | |
| Total | | 100.0 | 100.0 |
| (a)/(c) | | 3.0 | — |
| (c)/(d) | | 1.00 | — |
| (a)/(d) | | 3.00 | — |
| (a)/(b) | | 0.40 | 0.32 |
| Viscosity of composition for forming a coating film (25° C.) (Unit: mPa · s) | | 168.0 | 118.1 |
| Evaluation score | Spinning performance | B | C |
| | Scratch resistance | 4 | 2 |
| | Peelability of coating film composed of fibers | 3 | 1 |

*2) 99.5% Ethanol (manufactured by Wako Pure Chemical Corporation)
*3) PEG-400 (manufactured by Sanyo Chemical Industries, Ltd.)
*4) KF-96A-6CS (manufactured by Shin-Etsu Chemical Co., Ltd.)
*12) Baycusan C2000 (manufactured by Covestro AG)

The evaluation results are shown in Table 7. The results of Table 7 reveal that the coating films formed using the composition for forming a coating film used in each Example have good spinning stability, scratch resistance, and peelability of the coating films composed of fibers.

REFERENCE SIGNS LIST

10 Electrostatic spray apparatus
11 Low-voltage power supply
12 High-voltage power supply
13 Auxiliary electric circuit
14 Micro gear pump
15 Container
16 Nozzle
17 Pipeline
18 Flexible pipeline
19 Electric current limiting resistor
20 Housing

The invention claimed is:

1. A composition, comprising:
   (a) a polymer capable of forming a coating film;
   (b) at least one volatile substance selected from the group consisting of an alcohol and a ketone;
   (c) a plasticizer; and
   (d) a feel modifier other than the Component (c),
   wherein the composition is suitable for forming a coating film composed of fibers directly on the skin by an electrostatic spray,
   wherein said Component (d) comprises a silicone oil and at least one member selected from the group consisting of a hydrocarbon oil, an isononanoic acid ester, neopentyl glycol diethylhexanoate, and neopentyl glycol dicaprate.

2. The composition according to claim 1, having a viscosity of 2 mPa·s or more and 3,000 mPa·s or less at 25° C.

3. The composition according to claim 1, wherein a content mass ratio of the Component (a) to the Component (c), ((a)/(c)), is 0.033 to 300.

4. The composition according to claim 1, wherein a content mass ratio of the Component (a) to the Component (c), ((a)/(c)), is 0,80 to 20.

5. The composition according to claim 1, wherein a content mass ratio of the Component (c) to the Component (d), ((c)/(d)), is 0.0033 to 300.

6. The composition according to claim 1, wherein a content mass ratio of the Component (c) to the Component (d), ((c)/(d)), is 0.030 to 10.

7. The composition according to claim 1, wherein a content mass ratio of the Component (a) to the Component (b), ((a)/(b)), is 0.010 to 0.60.

8. The composition according to claim 1, wherein a content mass ratio of the Component (a) to the Component (b), ((a)/(b)), is 0.060 to 0.45.

9. The composition according to claim 1, wherein a content mass ratio of the Component (a) to the Component (d) is 0.033 to 300.

10. The composition according to claim 1, wherein a content mass ratio of the Component (a) to the Component (d) is 0.10 to 15.

11. The composition according to claim 1, wherein a content of the Component (a) is 1.0 mass % to 30 mass % and a content of the Component (b) is 50 mass % to 99 mass %.

12. The composition according to claim 1, wherein content of the Component (a) is 2.0 mass % to 35 mass % and a content of the Component (b) is 45 mass % to 97 mass %.

13. The composition according to claim 1, wherein a content of the Component (c) is 0.10 mass % to 30 mass % and a content of the Component (d) is 0.10 mass % to 30 mass %.

14. The composition according to claim 1, wherein a content of the Component (c) is 0.50 mass % to 30 mass % and a content of the Component (d) is 0.50 mass % to 40 mass %.

15. The composition according to claim 1, wherein the Component (a) is at least one selected from the group consisting of a partially saponified polyvinyl alcohol, a low saponified polyvinyl alcohol, a completely saponified polyvinyl alcohol, a polyvinyl butyral resin, a polyurethane resin, a polymethacrylate resin, an oxazoline-modified silicone, a polyvinyl acetal diethylamine acetate, and a polylactic acid.

16. The composition according to claim 1, wherein Component (c) is at least one selected from the group consisting of a polyol, a polyoxyalkylene glycol, a glycerin monofatty acid ester, a glycerin difatty acid ester, a malic acid diester, an N-acyl amino acid ester, ethylhexyl methoxycinnamate, and an alkyl benzoate.

17. A method for treating the skin, comprising:
   applying a composition to the skin by an electrostatic spraying device; and
   applying a skincare cosmetic to the skin by a device other than an electrostatic spraying device,
   wherein said composition comprises:
      (a) a polymer capable of forming a coating film;
      (b) at least one volatile substance selected from the group consisting of an alcohol and a ketone;
      (c) a plasticizer; and
      (d) a feel modifier other than the Component (c),
      wherein the composition is suitable for forming a coating film composed of fibers directly on the skin by an electrostatic spraying device.

18. The method according to claim 17, wherein said composition has a viscosity of 2 mPa·s or more and 3,000 mPa·s or less at 25° C.

19. The method according to claim 17, wherein a content mass ratio of the Component (a) to the Component (c), ((a)/(c)), is 0.033 to 300.

20. The method according to claim 17, wherein a content mass ratio of the Component (a) to the Component (c), ((a)/(c)), is 0.80 to 20.

21. The method according to claim 17, wherein a content mass ratio of the Component (c) to the Component (d), ((c)/(d)), is 0.0033 to 300.

22. The method according to claim 12, wherein a content mass ratio of the Component (c) to the Component (d), ((c)/(d)), is 0.030 to 10.

23. The method according to claim 17, wherein a content mass ratio of the Component (a) to the Component (b), ((a)/(b)), is 0.010 to 0.60.

24. The method according to claim 17, wherein a content mass ratio of the Component (a) to the Component (b), ((a)/(b)), is 0.060 to 0.45.

25. The method according to claim 17, wherein a content mass ratio of the Component (a) to the Component (d) is 0.033 to 300.

26. The method according to claim 17, wherein a content mass ratio of the Component (a) to the Component (d) is 0.10 to 15.

27. The method according to claim 17, wherein a content of the Component (a) is 1.0 mass % to 30 mass % and a content of the Component (b) is 50 mass % to 99 mass %.

28. The method according to claim 17 wherein a content of the Component (a) is 2.0 mass % to 35 mass % and a content of the Component (b) is 45 mass % to 97 mass %.

29. The method according to claim 17, wherein a content of the Component (c) is 0.10 mass % to 30 mass % and a content of the Component (d) is 0.10 mass % to 30 mass %.

30. The method according to claim 17, wherein content of the Component (c) is 0.50 mass % to 30 mass % and a content of the Component (d) is 0.50 mass % to 40 mass %.

31. The method according to claim 17, wherein the Component (a) is at least one member selected from the group consisting of a partially saponified polyvinyl alcohol, a low saponified polyvinyl alcohol a completely saponified polyvinyl alcohol, a polyvinyl butyral resin, a polyurethane resin, a polymethacrylate resin, an oxazoline-modified silicone, a polyvinyl acetal diethylamino acetate, and a polylactic acid.

32. The method according to claim 17, wherein the Component (c) is at least one member elected from the group consisting of a polyol, a polyoxyalkylene glycol, a glycerin monofatty acid ester, a glycerin difatty acid ester, a malic acid diester, an N-acyl amino acid ester, ethylhexyl methoxycinnamate, and an alkyl benzoate.

33. The method according to claim 17, wherein the Component (d) is at least one member selected front the group consisting of a silicone oil, a hydrocarbon oil, a palmitic acid ester, an isononanoic acid ester, neopentyl glycol diethylhexanoate, neopentyl glycol dicaprate, and an acyl amino acid diester.

34. The method according to claim 17, wherein the Component (d) is at least two members selected from the group consisting of a silicone oil, a hydrocarbon oil, an isononanoic acid ester, neopentyl glycol diethylhexanoate, and neopentyl glycol dicaprate.

35. The method according to claim 17, wherein the Component (d) comprises a silicone oil and at least one member selected from the group consisting of a hydrocarbon oil, an isononanoic acid ester, neopentyl glycol diethylhexanoate, and neopentyl glycol dicaprate.

* * * * *